(12) United States Patent
Langley et al.

(10) Patent No.: US 10,379,147 B2
(45) Date of Patent: Aug. 13, 2019

(54) APPARATUS AND METHOD FOR DETERMINING STATISTICAL MEAN AND MAXIMUM EXPECTED VARIANCE OF ELECTROMAGNETIC ENERGY TRANSMISSION BETWEEN COUPLED CAVITIES

(71) Applicants: Dassault Systemes Simulia Corp., Johnston, RI (US); Paul G. Bremner, Del Mar, CA (US)

(72) Inventors: Robin Stewart Langley, Cambridge (GB); Louis Kovalevsky, Cambridge (GB); Andrea Barbarulo, Paris (FR)

(73) Assignees: Dassault Systemes Simulia Corp., Johnston, RI (US); Paul G. Bremner, Del Mar, CA (US)

( * ) Notice: Subject to any disclaimer, the term of this patent is extended or adjusted under 35 U.S.C. 154(b) by 263 days.

(21) Appl. No.: 14/971,652

(22) Filed: Dec. 16, 2015

(65) Prior Publication Data

US 2016/0103165 A1 Apr. 14, 2016

Related U.S. Application Data

(63) Continuation of application No. PCT/US2014/043482, filed on Jun. 20, 2014, and a
(Continued)

(51) Int. Cl.
*G01R 23/16* (2006.01)
*G01V 3/165* (2006.01)
(Continued)

(52) U.S. Cl.
CPC ............. *G01R 23/16* (2013.01); *G01N 27/02* (2013.01); *G01R 13/02* (2013.01); *G01R 21/133* (2013.01);
(Continued)

(58) Field of Classification Search
None
See application file for complete search history.

(56) References Cited

U.S. PATENT DOCUMENTS 5,189,366 A 2/1993 Mayo
5,751,600 A 5/1998 Ochi et al.
(Continued)

FOREIGN PATENT DOCUMENTS

WO 2014205391 A1 12/2014

OTHER PUBLICATIONS

Langley, Robin S., "A Reciprocity Approach for Computing the Response of Wiring Systems to Diffuse Electromagnetic Fields", Nov. 17, 2010, IEEE Transactions on Electromagnetic Compatibility, vol. 52, No. 4, IEEE.
(Continued)

*Primary Examiner* — Steven B Gauthier
(74) *Attorney, Agent, or Firm* — Hamilton, Brook, Smith & Reynolds, P.C.

(57) ABSTRACT

Some embodiments include an apparatus for determining statistical mean and maximum expected of electromagnetic energy transmission between coupled cavities. Other embodiments of related apparatuses and methods are also disclosed.

18 Claims, 8 Drawing Sheets

Related U.S. Application Data continuation of application No. PCT/US2014/043492, filed on Jun. 20, 2014, said application No. PCT/US2014/043482 is a continuation-in-part of application No. 13/227,330, filed on Sep. 7, 2011, now Pat. No. 9,117,040, said application No. PCT/US2014/043492 is a continuation-in-part of application No. 13/227,330, filed on Sep. 7, 2011, now Pat. No. 9,117,040.

(60) Provisional application No. 61/838,091, filed on Jun. 21, 2013, provisional application No. 61/838,099, filed on Jun. 21, 2013, provisional application No. 61/474,367, filed on Apr. 12, 2011.

(51) Int. Cl.
| | | |
|---|---|---|
| *G01R 29/08* | (2006.01) | |
| *G06F 17/50* | (2006.01) | |
| *G01N 27/02* | (2006.01) | |
| *G01R 13/02* | (2006.01) | |
| *G01R 21/133* | (2006.01) | |
| *G06F 17/18* | (2006.01) | |

(52) U.S. Cl.
CPC ..... *G01R 29/0814* (2013.01); *G01R 29/0892* (2013.01); *G01V 3/165* (2013.01); *G06F 17/18* (2013.01); *G06F 17/5018* (2013.01); *G01V 2210/6163* (2013.01)

(56) References Cited

U.S. PATENT DOCUMENTS

| | | | |
|---|---|---|---|
| 10,156,599 | B2 | 12/2018 | Langley et al. |
| 2003/0019291 | A1 | 1/2003 | Pchelnikov et al. |
| 2006/0279273 | A1 | 12/2006 | Kazama |
| 2008/0097730 | A1 | 4/2008 | Canning |
| 2008/0127756 | A1 | 6/2008 | Horton et al. |
| 2008/0136189 | A1 | 6/2008 | Qu et al. |
| 2008/0276207 | A1 | 11/2008 | Suaya et al. |
| 2009/0167321 | A1* | 7/2009 | Krueger ............ G01R 29/0814 324/612 |
| 2010/0125438 | A1* | 5/2010 | Audet ................ G01R 29/0857 702/189 |
| 2012/0010836 | A1* | 1/2012 | Shemesh ........... G01R 29/0814 702/76 |
| 2012/0265464 | A1 | 10/2012 | Langley |
| 2014/0019050 | A1 | 1/2014 | Lambot |
| 2016/0103167 | A1 | 4/2016 | Langley et al. |

OTHER PUBLICATIONS

Langley, R. S., "On the Diffuse Field Reciprocity Relationship and Vibrational Energy Variance in a Random Subsystem at High Frequencies", Feb. 2007, Journal of Acoustic Society of America, Acoustic Society of America.

Shorter, P.J. et al., "On the Reciprocity Relationship Between Direct Field Radiation and Diffuse Reverberant Loading", Jan. 2005, Journal of Acoustic Society of America, Acoustic Society of America.

Andersen, J. Bach et al., "Room Electromagnetics", Apr. 2007, IEEE Antennas and Propagation Magazine, vol. 49, No. 2, IEEE.

Ishimaru, Akira et al., "Sommerfeld and Zenneck Wave Propagation for a Finely Conducting One-Dimensional Rough Surface", Sep. 2000, IEEE Transactions on Antennas and Propagation, vol. 48 No. 9, IEEE. Sep. 1, 2000.

International Search Report and Written Opinion for PCT/US2014/043482, 14 pages, dated Oct. 10, 2014.

International Search Report and Written Opinion for PCT/US2014/043492, 11 pages, dated Oct. 30, 2014.

Tesche, F.M., et al. "A Multiconductor Model for Determining the Response of Power Transmission and Distribution Lines to a High Altitude Electromagnetic Pulse (HEMP)," IEEE Transactions on Power Delivery, vol. 4, No. 3, 1989, pp. 1955-1964. doi:10,1109/61.32695.

MIL-STD-1310H, "Shipboard Bonding, Grouding, and Other Techniques for Electromagnetic Compatibility, Electromagnetic Pulse (EMP) Mitigation, and Sagety," 46 pages, Sep. 17, 2009.

MIL DTL 24643B, "Cables and Cords, Electric, Low Smoke, for Shipboard Use", 103 pages, Aug. 22, 2002.

Non-Final Office Action for U.S. Appl. No. 14/971,598, entitled "Apparatus and Method for Determining Statistics of Electric Current in an Electrical System Exposed to Diffuse Electromagnetic Fields," dated Oct. 17, 2017.

Notice of Allowance for U.S. Appl. No. 14/971,598, entitled "Apparatus and Method for Determining Statistical Mean and Maximum Expected Variance of Electromagnetic Energy Transmission Between Coupled Cavities", dated Sep. 11, 2018.

Final Office Action for U.S. Appl. No. 14/971,598, entitled: "Apparatus and Method for Determining Statistics of Electric Current in an Electrical System Exposed to Diffuse Electromagnetic Fields," dated Mar. 16, 2018.

* cited by examiner

APPARATUS AND METHOD FOR DETERMINING STATISTICAL MEAN AND MAXIMUM EXPECTED VARIANCE OF ELECTROMAGNETIC ENERGY TRANSMISSION BETWEEN COUPLED CAVITIES

CROSS-REFERENCE TO RELATED APPLICATIONS

This application is a continuation application of International Patent Application No. PCT/US2014/043482, filed Jun. 20, 2014, and is a continuation application of International Patent Application No. PCT/US2014/043492, filed Jun. 20, 2014. International Patent Application No. PCT/US2014/043482 and International Patent Application No. PCT/US2014/043492 each claim the benefit of U.S. Provisional Application No. 61/838,091, filed Jun. 21, 2013, and U.S. Provisional Application No. 61/838,099, filed Jun. 21, 2013. Meanwhile, International Patent Application No. PCT/US2014/043482 and International Patent Application No. PCT/US2014/043492 each are a continuation-in-part application of U.S. patent application Ser. No. 13/227,330, filed Sep. 7, 2011, which claims priority from of U.S. Provisional Patent Application No. 61/474,367, filed Apr. 12, 2011. International Patent Application No. PCT/US2014/043482 and International Patent Application No. PCT/US2014/043492, U.S. Provisional Application No. 61/838,091, U.S. Provisional Application No. 61/838,099, U.S. patent application Ser. No. 13/227,330, and U.S. Provisional Patent Application No. 61/474,367 each are incorporated herein by reference in their entirety.

FIELD OF THE INVENTION

This invention relates generally to apparatuses and methods for modeling and analyzing electromagnetic fields in an electrical system, and relates more particularly to apparatuses and methods for determining statistical mean and maximum expected energy transmission between coupled cavities by modeling and analyzing the electromagnetic fields in the electrical system.

DESCRIPTION OF THE BACKGROUND

Many situations can exist in which electromagnetic fields can induce electric currents in an electrical system, such as, for example, an electrical system of a vehicle (e.g., an automobile, an aircraft, a ship, etc.) or an immobile structure (e.g., a building). For example, mobile phone transmitters, Bluetooth® transmitters, and electromagnetic pulse weapons are each potential sources of electromagnetic fields able to induce electric currents in the electrical system. These induced electric currents can potentially damage and/or interfere with the electrical system. Computationally analyzing electrical systems prior to implementation can permit electromagnetic fields in electrical systems to be modeled so that the electrical system can be designed to mitigate or eliminate formation of such induced electrical currents in order to protect the integrity of the electrical system. However, using a direct deterministic calculation to model the electromagnetic fields can be inefficient and/or less than realistic.

Accordingly, improved apparatuses and methods for modeling and analyzing electromagnetic fields in an electrical system are needed.

BRIEF DESCRIPTION OF THE DRAWINGS

To facilitate further description of the embodiments, the following drawings are provided in which.

Figure 1:
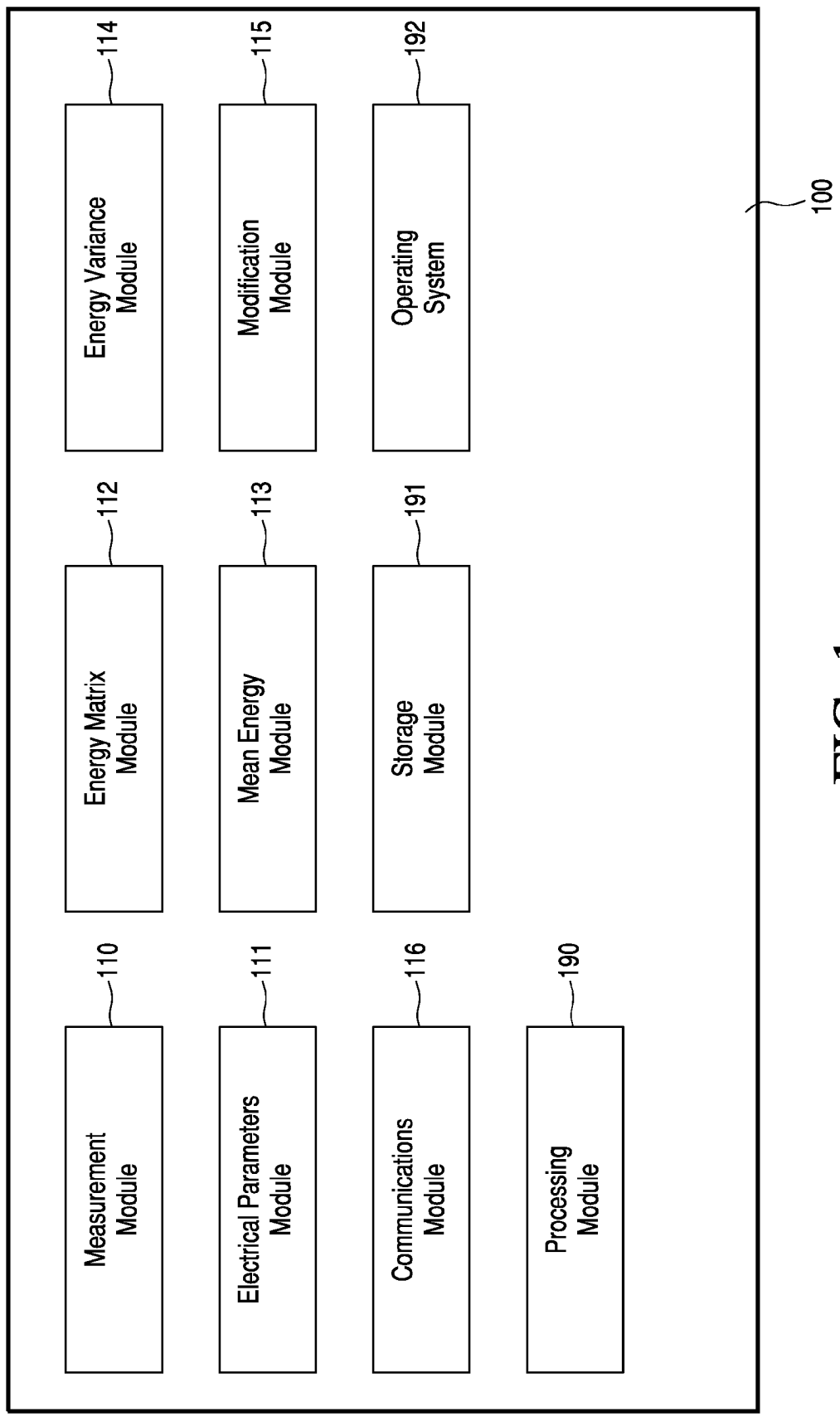
FIG. 1 illustrates a representative block diagram of an apparatus configured to determine (e.g., model and/or analyze) one or more electromagnetic fields in one or more first cavities of an electrical system and one or more second cavities of the electrical system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments include an apparatus configured to determine one or more parameters related to one or more electromagnetic fields in a first cavity coupled to a second cavity. At least one electromagnetic wave creation element is located in the second cavity, and an electrical system can comprise the first cavity, the second cavity, and the at least one electromagnetic wave creation element. The apparatus comprises a processing module and a non-transitory memory storage module operable to store computer instructions configured to run on the processing module. The computer instructions can be configured to perform acts of: receiving two or more measurement parameters related to the first cavity and the second cavity; receiving one or more electrical parameters of the at least one electromagnetic wave creation element; determining an energy matrix of the one or more electromagnetic fields in the first cavity and the second cavity; determining a mean energy of the one or more electromagnetic fields in the first cavity and the second cavity; and determining an energy variance of the one or more electromagnetic fields in the first cavity and the second cavity.

Further embodiments include a method of determining one or more electromagnetic fields in a first cavity coupled to a second cavity. At least one electromagnetic wave creation element is located in the second cavity and an electrical system can comprise the first cavity, the second cavity, and the at least one electromagnetic wave creation element. The method can comprise: determining two or more physical parameters of the first cavity and the second cavity; determining one or more electrical parameters of the at least one electromagnetic wave creation element; executing one or more first computer instructions configured to determine an energy matrix for the electrical system; executing one or more second computer instructions configured to determine a mean energy of the one or more electromagnetic fields in the first cavity and the second cavity; and executing one or more third computer instructions configured to determine an energy variance of the one or more electromagnetic fields in the first cavity and the second cavity. The one or more first computer instructions, the one or more second computer instructions, and the one or more third computer instructions can be configured to run at a processing module and configured to be stored at a non-transitory memory storage module.

Other embodiments include a method of determining one or more electromagnetic fields in a first cavity coupled to a second cavity. At least one electromagnetic wave creation element can be located in the second cavity, and an electrical system can comprise the first cavity, the second cavity, and the at least one electromagnetic wave creation element. The method can comprise: executing one or more first computer instructions configured to determine two or more physical parameters of the first cavity and the second cavity; executing one or more second computer instructions configured to determine one or more electrical parameters of the at least one electromagnetic wave creation element; executing one or more third computer instructions configured to determine a mean energy of the one or more electromagnetic fields in the first cavity and the second cavity; executing one or more fourth computer instructions configured to determine an energy variance of the one or more electromagnetic fields in the first cavity and the second cavity; executing one or more fifth computer instructions configured to use the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element; and executing one or more sixth computer instructions configured to model the one or more potential changes. The one or more first computer instructions, the one or more second computer instructions, the one or more third computer instructions, the one or more fourth computer instructions, the one or more fifth computer instructions, and the one or more sixth computer instructions are configured to run at a processing module and configured to be stored at a non-transitory memory storage module.

Some embodiments include a method of determining one or more electromagnetic fields in a first cavity coupled to a second cavity. At least one electromagnetic wave creation element is located in the second cavity, and an electrical system comprises the first cavity, the second cavity, and the at least one electromagnetic wave creation element. The method can comprise: determining two or more physical parameters of the first cavity and the second cavity; determining one or more electrical parameters of the at least one electromagnetic wave creation element; using a processing module to determine an energy matrix for the electrical system; using the processing module to determine a mean energy of the one or more electromagnetic fields in the first cavity and the second cavity; and using the processing module to determine an energy variance of the one or more electromagnetic fields in the first cavity and the second cavity.

Further embodiments include an apparatus configured to use a processing module to determine one or more parameters related to one or more electromagnetic fields in a first cavity coupled to a second cavity. At least one electromagnetic wave creation element is located in the second cavity, and an electrical system can comprise the first cavity, the second cavity, and the at least one electromagnetic wave creation element. The apparatus comprises a measurement module, an electrical parameters module, an energy matrix module, a mean energy module, and an energy variance module, each of which can be configured to run on the processing module. The measurement module can be configured to receive two or more measurement parameters related to the first cavity and the second cavity. Meanwhile, the electrical parameters module can be configured to receive one or more electrical parameters of the at least one electromagnetic wave creation element. Further, the energy matrix module can be configured to determine the energy matrix of the one or more electromagnetic fields in the first cavity and the second cavity. Further still, the mean energy module can be configured to determine a mean energy of the one or more electromagnetic fields in the first cavity and the second cavity. Also, the energy variance module can be configured to determine an energy variance of the one or more electromagnetic fields in the first cavity and the second cavity.

Other embodiments include a method of determining one or more electromagnetic fields in a first cavity coupled to a second cavity. At least one electromagnetic wave creation element is located in the second cavity, and an electrical system comprises the first cavity, the second cavity, and the at least one electromagnetic wave creation element. The method can comprise: determining two or more physical parameters of the first cavity and the second cavity; determining one or more electrical parameters of the at least one electromagnetic wave creation element; using the processing module to determine a mean energy of the one or more electromagnetic fields in the first cavity and the second cavity; using the processing module to determine an energy variance of the one or more electromagnetic fields in the first cavity and the second cavity; and using the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element.

As a preliminary matter, embodiments of the apparatuses and methods described herein can build upon the teachings of U.S. patent application Ser. No. 13/227,330. As noted in the description of the background above, electric currents induced in an electrical system by electromagnetic waves can potentially damage the electrical system. A characteristic of this type of problem is that a source of electromagnetic excitation can produce an electromagnetic field inside a cavity, which can then damage and/or interfere with the electrical system. In many examples, a frequency of the electromagnetic excitation is relatively high, in that the electromagnetic wavelength is short in comparison to the dimensions of the cavity. For example, a typical mobile phone transmitter can produce electromagnetic excitation at around 2 Gigahertz (GHz) and a wavelength of 15 centimeters (cm), meaning that an electromagnetic field produced within a typical cabin of a vehicle (e.g., an automobile, an aircraft, a ship, etc.) will have a spatially complex distribution.

Theoretically, an electromagnetic field in an electrical system can be predicted numerically by solving Maxwell's equations for the electrical system, using either a finite element analysis or the finite difference analysis to capture the detailed spatial distribution of the electromagnetic fields. However, to calculate the electromagnetic fields using such a deterministic analysis can require a large amount of computing power and a large amount of storage. That is, a deterministic analysis can require computational analysis of many grid points (e.g., millions of grid points). In one example, fifteen million grid points (i.e., degrees of freedom) were used to calculate the electromagnetic fields for a single cavity in an exemplary automobile.

Another feature of short wavelength electromagnetic excitation is that the response of an electrical system can be very sensitive to small changes. For example, moving a wire harness by several centimeters can significantly change the resulting electromagnetic fields in an electrical system. Accordingly, when using a deterministic model, it may be necessary to completely remodel an electrical system when any small change is made to the electrical system.

In view of the limitations of deterministic analysis, notably, it has been determined that a short wavelength electromagnetic field inside a cavity of a vehicle or immobile structure can be well approximated as an ideal diffuse wave field. Taking advantage of this determination, the apparatuses and methods described herein can approximate the electromagnetic waves in an electrical system more efficiently than a direct deterministic analysis by analyzing the electromagnetic waves as ideal diffuse wave fields, while also being more realistic from a statistical point of view.

Figure 2:
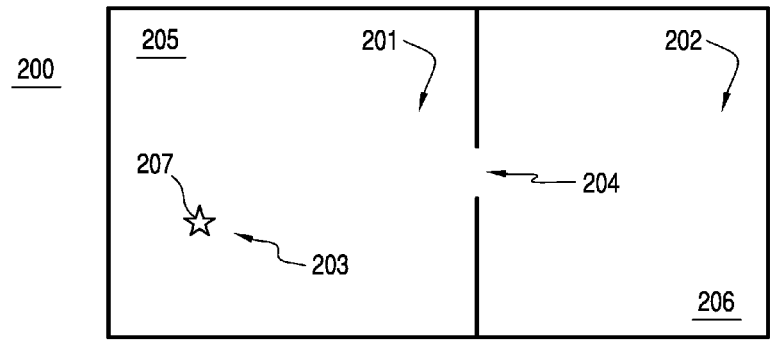
FIG. 2 illustrates a representative block diagram of an exemplary electrical system, according to an embodiment.

Turning now to the drawings, FIG. 1 illustrates a representative block diagram of an apparatus 100 configured to determine (e.g., model and/or analyze) one or more electromagnetic fields in one or more first cavities of an electrical system and one or more second cavities of the electrical system, according to an embodiment. The electromagnetic field(s) can be caused by one or more electromagnetic waves emitted by at least one electromagnetic wave creation element of the electrical system. Apparatus 100 is merely exemplary and is not limited to the embodiments presented herein. Apparatus 100 can be employed in many different embodiments or examples not specifically depicted or described herein. In some embodiments, the electrical system can be similar or identical to an electrical system 200 (FIG. 2), as described in greater detail below. The one or more first cavities can be similar or identical to one or more first cavities 201 (FIG. 2); and/or the one or more second cavities can be similar or identical to one or more second cavities 202 (FIG. 2). Apparatus 100 can be operable to determine one or more parameters (e.g., a statistical mean energy and/or a maximum energy variance of the electromagnetic field(s) in each cavity of the one or more first cavities and/or one or more second cavities, confidence bands for maximum energy of the electromagnetic field(s) in each cavity of the one or more first cavities and/or one or more second cavities, etc.).

Turning to the next drawing, FIG. 2 illustrates a representative block diagram of an exemplary electrical system 200, according to an embodiment. Electrical system 200 can comprise one or more first cavities 201 (e.g., cavity 205) and/or one or more second cavities 202 (e.g., cavity 206). Further, electrical system 200 can comprise at least one electromagnetic wave creation element 203 (e.g., electromagnetic wave creation element 207). In many embodiments, one or more first cavities 201 (e.g., cavity 205) and one or more second cavities 202 (e.g., cavity 206) can be coupled together, such as, for example, by a shared wall and/or by one or more apertures (e.g., aperture 204). Accordingly, in these or other embodiments, electrical system 200 can comprise aperture 204. In many embodiments, at least one electromagnetic wave creation element of electromagnetic wave creation element(s) 203 (e.g., electromagnetic wave creation element 207) can be located at one or more first cavities 201 (e.g., cavity 205).

Although FIG. 2 illustrates one or more first cavities 201 and/or one or more second cavities 202 as comprising only two cavities (e.g., cavity 205 and cavity 206), in other embodiments, one or more first cavities 201 and/or one or more second cavities 202 each can comprise any suitable quantity of cavities (e.g., two cavities, three cavities, etc.). In these or other embodiments, one or more first cavities 201 and one or more second cavities 202 can be directly or indirectly coupled together, such as, for example, by any suitable number of shared walls and/or by any suitable number of apertures (e.g., aperture 204). For purposes of illustration, assuming one or more first cavities 201 comprise multiple cavities, one cavity of the multiple cavities can be directly coupled to another one of the multiple cavities, which can then be directly coupled to one or more second cavities 202 so that the former cavity indirectly couples with one or more second cavities 202. Further, in various embodiments, any cavities of one or more first cavities 201 and/or one or more second cavities 202 can be coupled together by more than one aperture (e.g., aperture 204). The apertures (e.g., aperture 204) coupling one or more first cavities 201 (e.g., cavity 205) and/or one or more second cavities 202 (e.g., cavity 206) can comprise any type of aperture. In some specific examples, the apertures (e.g., aperture 204) can comprise one or more doors, windows, holes, cracks, etc.

In some embodiments, one or more first cavities 201 (e.g., cavity 205) can comprise one or more first cabins, compartments, rooms, etc. of a vehicle (e.g., an automobile, a ship, an aircraft, etc.); and one or more second cavities 202 (e.g., cavity 206) can comprise one or more second cabins, compartments, rooms, etc. of the vehicle. For example, one or more first cavities 201 (e.g., cavity 205) can comprise an aircraft cockpit of an aircraft and one or more second cavities 202 (e.g., cavity 206) can comprise an aircraft cabin of the aircraft. In another example, one or more first cavities 201 (e.g., cavity 205) can comprise a first room of a ship and one or more second cavities 202 (e.g., cavity 206) can comprise a second room of the ship. In a further example, one or more first cavities 201 (e.g., cavity 205) can comprise an exterior region of an aircraft and one or more second cavities 202 (e.g., cavity 206) can comprise an interior of the aircraft. In still another example, one or more first cavities 201 (e.g., cavity 205) can comprise a first compartment of an automobile and one or more second cavities 202 (e.g., cavity 206) can comprise a second compartment of the automobile.

In other embodiments, one or more first cavities 201 (e.g., cavity 205) can comprise one or more first compartments, rooms, etc. of an immobile structure (e.g., a commercial building or a house); and one or more second cavities 202 (e.g., cavity 206) can comprise one or more second compartments, rooms, etc. of the immobile structure.

In many embodiments, electromagnetic wave creation element(s) 203 (e.g., electromagnetic wave creation element 207) can comprise one or more sources of electromagnetic radiation. That is, electromagnetic wave creation element(s) 203 (e.g., electromagnetic wave creation element 207) can be configured to emit electrical waves. Exemplary electromagnetic wave creation element(s) 203 (e.g., electromagnetic wave creation element 207) can comprise a mobile communication device (e.g., a mobile phone transmitter, a Bluetooth® transmitter, etc.), an electromagnetic pulse weapon, lightning, and/or any other electromagnetic source suitably configured to emit electrical waves.

Turning now back to FIG. 1, in many embodiments, apparatus 100 can refer to an electromagnetic field modeling apparatus (i.e. a electromagnetic field modeling system). In various embodiments, apparatus 100 can comprise a computer system. The computer system can be similar or identical to computer system 1300 (FIG. 13), as described below.

Accordingly, in these or other embodiments, apparatus 100 can comprise a processing module 190, a communications module 116, a storage module 191, and an operating system module 192. Further, apparatus 100 can comprise a measurement module 110, an electrical parameters module 111, an energy matrix module 112, a mean energy module 113, an energy variance module 114, and a modification module 115. In some embodiments, part or all of processing module 190, communications module 116, storage module 191, and/or operating system module 192 can be omitted.

In implementation, processing module 190 can comprise one or more processors. As used herein, a "processor" can mean any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions (e.g., running computer software).

Meanwhile, storage module 191 can comprise one or more non-volatile computer memory storage devices configured to store computer software (e.g., computer instructions) and/or data (e.g., data related to apparatus 100 and/or electrical system 200 (FIG. 2)) on a temporary and/or permanent basis for use by apparatus 100 and/or processing module 190. Notably, apparatus 100 can also include one or more volatile computer memory storage devices.

In many embodiments, at least part of measurement module 110, electrical parameters module 111, energy matrix module 112, mean energy module 113, energy variance module 114, modification module 115, communications module 116, and/or operating system module 192 can be implemented as computer software. Accordingly, in these or other embodiments, at least part of measurement module 110, electrical parameters module 111, energy matrix module 112, mean energy module 113, energy variance module 114, modification module 115, communications module 116, and/or operating system module 192 can be configured to run at processing module 190 and/or to be stored at storage module 191. In some embodiments, at least part of measurement module 110, electrical parameters module 111, energy matrix module 112, mean energy module 113, energy variance module 114, modification module 115, communications module 116, and/or operating system module 192 can also be configured to be stored at the volatile computer memory storage devices of apparatus 100 as may be necessary to performed the desired functions of apparatus 100.

Communications module 116 can be configured to permit communication between processing module 190 and storage module 191, and between apparatus 100 and one or more users of apparatus 100. For example, communications module 116 can permit processing module 190 to call computer software (e.g., at least part of measurement module 110, electrical parameters module 111, energy matrix module 112, mean energy module 113, energy variance module 114, modification module 115, communications module 116, and/or operating system module 192) stored at storage module 191 and/or data stored at storage module 191 for operation of apparatus 100. Further, communications module 116 can permit data calculated by processing module 190 to be communicated to storage module 191 for storage. Further still, communications module 116 can permit any user(s) of apparatus 100 to provide inputs (e.g., commands) to processing module 190 and/or storage module 191, and can provide data calculated by processing module 190 to be output to the user(s). The input(s) can be provided by any suitable input mechanism(s) (e.g., a keyboard, mouse, etc.) and the output(s) can be provided at any suitable output mechanism(s) (e.g., displays, speakers, etc.). Notably, the input and/or output mechanism(s) can be integral with apparatus 100 or can be partially or entirely part of another apparatus, such as, for example, another computer system.

Although at least part of communications module 116 can be implemented as computer software, at least part of communications module 116 can also be implemented as any suitable hardware configured to perform the desired communication for apparatus 100. For example, communications module 116 can comprise (a) one or more transmission components configured to provide wired communication (e.g., one or more data buses, such as, for example, universal serial bus(es); one or more networking cables, such as, for example, coaxial cable(s), optical fiber cable(s), and/or twisted pair cable(s); any other suitable data cable, etc.) and/or (b) one or more transmission components configured to provide wireless communication (e.g., one or more radio transceivers, one or more infrared transceivers, etc.). Also, communications module 116 can comprise one or more networking components (e.g., modulator-demodulator components, gateway components, etc.). Further, communications module 116 can be configured to operate using any one or any combination of wired and/or wireless communication network topologies (e.g., ring, line, tree, bus, mesh, star, daisy chain, hybrid, etc.) and/or protocols (e.g., personal area network (PAN) protocol(s), local area network (LAN) protocol(s), wide area network (WAN) protocol(s), cellular network protocol(s), Powerline network protocol(s), etc.). Exemplary PAN protocol(s) can comprise Bluetooth, Zigbee, Wireless Universal Serial Bus (USB), Z-Wave, etc.; exemplary LAN and/or WAN protocol(s) can comprise Institute of Electrical and Electronic Engineers (IEEE) 802.3, IEEE 802.11, etc.; and exemplary wireless cellular network protocol(s) can comprise Global System for Mobile Communications (GSM), General Packet Radio Service (GPRS), Code Division Multiple Access (CDMA), Evolution-Data Optimized (EV-DO), Enhanced Data Rates for GSM Evolution (EDGE), 3GSM, Digital Enhanced Cordless Telecommunications (DECT), Digital AMPS (IS-136/Time Division Multiple Access (TDMA)), Integrated Digital Enhanced Network (iDEN), etc. The software and/or hardware of communications module 116 can be dependent on the network topologies and/or protocols in use, and vice versa.

In various embodiments, operating system 192 can comprise computer software configured to manage the hardware and computer software resources of a computer and/or a computer network. Operating system 192 can perform basic tasks such as, for example, controlling and allocating memory, prioritizing the processing of instructions, controlling input and output devices, facilitating networking, and managing files. Examples of common operating systems for a computer include Microsoft® Windows, Mac® operating system (OS), UNIX® OS, and Linux® OS.

In some embodiments, when apparatus 100 comprises a computer system, the computer system can comprise a single computer, a single server, or a cluster or collection of servers. Typically, a cluster or collection of servers can be used when the demands by apparatus 100 are beyond the reasonable capability of a single computer or a single server. In many embodiments, the servers in the cluster or collection of servers are interchangeable from the perspective of the users.

Meanwhile, although processing module 190, communications module 116, storage module 191, operating system module 192, measurement module 110, electrical parameters module 111, energy matrix module 112, mean energy module 113, energy variance module 114, and/or modification module 115 are described herein generally as being located at part of a single computer or server, in many embodiments, parts of any of processing module 190, communications module 116, storage module 191, operating system module 192, measurement module 110, electrical parameters module 111, energy matrix module 112, mean energy module 113, energy variance module 114, and/or modification module 115 may be spread between and/or possibly overlap at multiple servers when the computer system of apparatus 100 comprises a cluster of collection of servers. For example, the computer system of apparatus 100 can comprise a first server comprising a first portion of one or more of processing module 190, communications module 116, storage module 191, operating system module 192, measurement module 110, electrical parameters module 111, energy matrix module 112, mean energy module 113, energy variance module 114, and/or modification module 115. Meanwhile, one or more second servers can comprise a second, possibly overlapping, portion of processing module 190, communications module 116, storage module 191, operating system module 192, measurement module 110, electrical parameters module 111, energy matrix module 112, mean energy module 113, energy variance module 114, and/or modification module 115.

In operation of apparatus 100, measurement module 110 can be configured to receive one or more (e.g., two or more) physical parameters of the one or more first cavities and one or more second cavities of the electrical system. In these or other embodiments, the physical parameters of the one or more first cavities and one or more second cavities of the electrical system can comprise: (a) one or more physical properties (e.g., dimensions, etc.) of the one or more first cavities and one or more second cavities of the electrical system and/or (b) one or more properties (e.g., reflective properties) of one or more surfaces of and/or surface coatings (e.g., paint, wallpaper, flooring material like carpet, tile, laminate, linoleum, etc., ceiling materials, etc.) on at least one of the surface(s) of the one or more first cavities and one or more second cavities of the electrical system. Notably, the reflective properties of the surface(s) of and/or coatings on the surface(s) of the one or more first cavities and/or one or more second cavities can effect and change the electromagnetic field(s). Accordingly, these reflective properties can be determined for each frequency of interest (e.g., 250 MHz, 9 GHz, etc.) of the electromagnetic waves to increase accuracy of apparatus 100. Further, when applicable, measurement module 110 can be configured to receive physical parameters (e.g., reflective properties) of one or more objects (e.g., furniture, etc.) within the one or more first cavities and one or more second cavities of the electrical system. Similar to the surface(s) and/or coating(s), the reflective properties of the object(s) can also effect and change the electromagnetic field(s) so that accounting for the object(s) can also increase accuracy of apparatus 100.

In these or other embodiments, when applicable, measurement module 110 can be configured to receive physical parameters of the aperture(s) coupling the one or more first cavities and one or more second cavities of the electrical system. In these or other embodiments, the physical parameters of the one or more first cavities and one or more second cavities of the electrical system can comprise one or more physical properties (e.g., dimensions) of the aperture(s) of the electrical system.

In some embodiments, and for some physical parameters of the one or more first cavities, one or more second cavities, object(s), and/or aperture(s) of the electrical system, apparatus 100 can receive the physical parameters of the one or more first cavities, one or more second cavities, object(s), and/or aperture(s) of the electrical system through communication with one or more sensors configured to measure the physical parameter(s) or a user of apparatus 100 can provide the physical parameters by manual entry. When the user manually enters the physical parameter(s), the user may physically measure the physical parameters (e.g., using sensors and/or measurement devices, such as, for example, calipers, tape measures, etc.) and/or use reference materials related to the electrical system (e.g., schematics, blueprints, architectural drawings, etc.) to obtain the physical parameter(s).

Further, in many embodiments, electrical parameters module 111 can be configured to receive one or more electrical parameters of the electromagnetic wave creation element(s) of the electrical system. In these or other embodiments, the electrical parameters of the electromagnetic wave creation element(s) can comprise (a) one or more electric powers of electromagnetic waves emitted by the electromagnetic wave creation element(s) at one or more frequencies, (b) the one or more frequencies of the electromagnetic waves, and/or (c) one or more wave lengths of the electromagnetic waves. Electrical parameters module 111 can receive the electrical parameters of the electromagnetic wave creation element(s) of the electrical system through communication with one or more sensors configured to measure the electrical parameter(s) or a user of apparatus 100 can provide the electrical parameters by manual entry. When the user manually enters the electrical parameter(s), the user may physically measure the electric power(s) and/or frequencies of the electromagnetic waves emitted by the electromagnetic wave creation element(s) (e.g., using sensors) and/or use reference materials related to the electromagnetic wave creation element(s) to obtain the power(s), wavelength(s) and/or one or more frequencies.

In many embodiments, when measurement module 110 and/or electrical parameters module 111 receive the physical properties of the conductive element(s) of the electrical system and/or the electrical parameter(s) of the electromagnetic wave creation element(s) of the electrical system, respectively, the physical properties and/or the electrical parameter(s) can be stored at storage module 191. Meanwhile, energy matrix module 112, mean energy module 113, energy variance module 114, and/or modification module 115 can access the physical properties and/or the electrical parameter(s) directly or as stored at storage module 191 as necessary to perform their functionality.

Meanwhile, in further operation of apparatus 100, energy matrix module 112 can be configured to determine (e.g., calculate) an energy matrix for the electrical system; mean energy module 113 can be configured to determine (e.g., calculate) a mean (e.g., statistical mean) energy of the electromagnetic field(s) in the one or more first cavities and one or more second cavities of the electrical system (e.g., each cavity of the one or more first cavities and one or more second cavities of the electrical system); and/or energy variance module 114 can be configured to determine (e.g., calculate) an energy variance (e.g., maximum energy variance) of the electromagnetic field(s) in the one or more first cavities and one or more second cavities of the electrical system (e.g., each cavity of the one or more first cavities and one or more second cavities of the electrical system). Notably, the particular manner of operation of energy matrix module 112, mean energy module 113, and energy variance module 114 can depend on the complexity of the electrical system, as discussed below. These varying manners of operation of energy matrix module 112, mean energy module 113, and energy variance module 114 are discussed below.

The energy matrix for the electrical system determined by energy matrix module 112 can be expressed in a generalized form where the electrical system comprises only one cavity of the one or more first cavities coupled to only one cavity of the one or more second cavities as follows:

$$\begin{pmatrix} \omega\beta_i n_i + \omega\beta_{ij} n_i & -\omega\beta_{ij} n_i \\ -\omega\beta_{ji} n_j & \omega\beta_j n_j + \omega\beta_{ji} n_j \end{pmatrix} \quad (1)$$

wherein $\omega$ is the frequency, $n_i$ is the modal density of the ith cavity centered on $\alpha$ and $n_j$ is the modal density of the jth cavity centered on $\alpha$, $\beta_i$ is the loss factor of the cavity for ith cavity and $\beta_j$ is the loss factor of the cavity for jth cavity, and $\beta_{ij}$ and $\beta_{ji}$ are the coupling loss factor between the ith cavity and the jth cavity. As discussed in greater detail below, mean energy module 113 can use the energy matrix determined by energy matrix module 112 to determine the mean energy of the electromagnetic field(s) in the one cavity of the one or more first cavities and the one cavity of the one or more second cavities of the electrical system using Equation (25). Further, energy variance module 114 can use the energy matrix determined by energy matrix module 112 and the mean energy of the electromagnetic field(s) in the one cavity of the one or more first cavities and the one cavity of the one or more second cavities of the electrical system to determine the energy variance of the electromagnetic field(s) in the one cavity of the one or more first cavities and the one cavity of the one or more second cavities of the electrical system using Equation (31).

For ease of illustration, the functionality of energy matrix module 112, mean energy module 113, and energy variance module 114 is discussed primarily with respect to the foregoing simplified electrical system comprising only one cavity of the one or more first cavities coupled to only one cavity of the one or more second cavities. However, as discussed in greater detail below, Equation (39) expands the energy matrix of Equation (1), Equation (40) expands the mean energy calculation of Equation (25), and Equation (41) expands the energy variance calculation of Equation (31) so that electrical systems comprising any number of cavities (e.g., N cavities) arranged with any suitable coupling arrangements can be accommodated.

Energy matrix module 112 can determine the loss factor (e.g., $\beta_i$ and $\beta_j$) for each cavity of the one or more first cavities and for each cavity of the one or more second cavities (e.g., the one cavity of the one or more first cavities and the one cavity of the one or more second cavities) in order to determine the energy matrix for the electrical system. In these or other embodiments, the loss factor (e.g., $\beta_i$ and $\beta_j$) for a particular cavity of the one or more first cavities and the one or more second cavities can be the inverse of a quality factor (Q-factor) (e.g., $\beta_i=1/Q_i$; $\beta_j=1/Q_j$) of the particular cavity of the one or more first cavities and the one or more second cavities. The quality factor (e.g., $Q_i$ and $Q_j$) can be received by energy matrix module 112 as known data (e.g., provided by reference materials) or can be determined (e.g., calculated, such as, for example, using Equation (6)) from the absorption properties of the cavity walls of the particular cavity of the one or more first cavities and the one or more second cavities.

Further, energy matrix module 112 to determine a cavity modal density (e.g., $n_i$ and $n_j$) for each cavity of the one or more first cavities and the one or more second cavities (e.g., the one cavity of the one or more first cavities and the one cavity of the one or more second cavities) in order to determine the energy matrix for the electrical system. The cavity modal density of a particular cavity can be defined as the average number of natural frequencies which fall within a unit frequency band centered on the frequency $\alpha$. For example, the cavity modal density for the ith cavity and this can be written as:

$$n_i = \frac{V_i \omega^2}{\pi^2 c^3}, \tag{2}$$

where c is the speed of light. A comparable relationship can be written for the jth cavity replacing a j subscript for each i subscript of Equation (2).

In many embodiments, energy matrix module 112 can be operable to determine coupling loss factors (e.g., $\beta_{ij}$ and $\beta_{ji}$) for each coupled pair of cavities of the one or more first cavities and the one or more second cavities that are directly coupled together (e.g., the one cavity of the one or more first cavities and the one cavity of the one or more second cavities) in order to determine the energy matrix for the electrical system. The following paragraphs discuss the manner by which energy matrix module 112 calculates the coupling loss factors first for transmission through a shared cavity wall (e.g., membrane), and then for the transmission through one or more apertures in a shared cavity wall. Equation (27) below also provides a relationship between coupling loss factors (e.g., $\beta_{ij}$ and $\beta_{ji}$).

Figure 3:
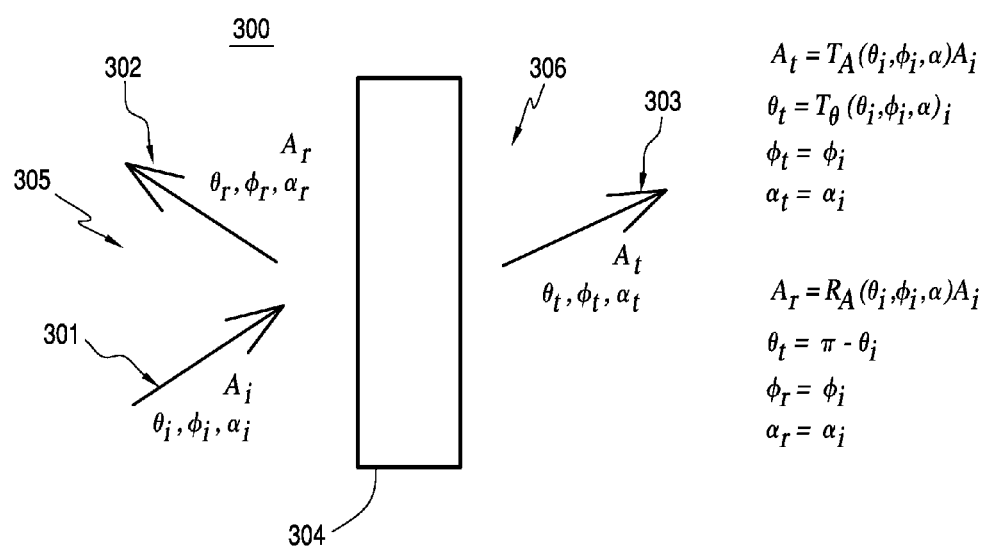
FIG. 3 illustrates a representative diagram of a transmitted electromagnetic wave in a first cavity and a reflected electromagnetic wave in a second cavity resulting from an incident electromagnetic wave in the first cavity coming in contact with a shared cavity wall of an electrical system of the type of FIG. 2.

For coupling loss factors through a shared cavity wall, energy matrix module 112 can apply a wave approach. FIG. 3 illustrates a representative diagram of a transmitted electromagnetic wave 302 in a first cavity 305 and a reflected electromagnetic wave 303 in a second cavity 306 resulting from an incident electromagnetic wave 301 in first cavity 305 coming in contact with a shared cavity wall 304 of an electrical system 300. The electrical system can be similar or identical to electrical system 200 (FIG. 2). Accordingly, first cavity 305 can be similar or identical to one cavity of one or more first cavities 201 (FIG. 2), and second cavity 306 can be similar or identical to one or more second cavities 202 (FIG. 2). The transmitted electromagnetic wave 302, reflected electromagnetic wave 303, and incident electromagnetic wave 301 are expressed in a spherical coordinate system where $\theta$ represents the polar angle, $\varphi$ represents the azimuthal angle, a represents the polarization angle, and A represents the amplitude of the respective electromagnetic waves. Various relationships of the coordinates of the transmitted electromagnetic wave 302 and the reflected electromagnetic wave 303 are expressed as a function of the incident electromagnetic wave 301 where T represents a wave amplitude transmission coefficient and R represents a wave amplitude reflection coefficient of the incident electromagnetic wave 301 with respect to shared cavity wall 304 for a particular spherical orientation of the incident electromagnetic wave 301.

Returning to FIG. 1, by describing the electromagnetic field(s) as uniform distributions of uncorrelated waves over all directions and polarizations, as illustrated by FIG. 3, the coupling loss factor $\beta_{ij}$ from cavity i to cavity j can be determined by energy matrix module 112 as follows:

$$\beta_{ij} = \frac{c_i A_{ij} \langle \tau_{ij} \rangle}{4 \omega V_i}, \tag{3}$$

where $c_i$ refers to the speed of light in the ith cavity, $A_{ij}$ refers to the effective (e.g., shared) area (e.g., approximate effective area) of the shared cavity wall, $\langle \tau_{ij} \rangle$ refers to the diffuse electromagnetic field power transmission coefficient of the electromagnetic wave(s), and $V_i$ refers to the volume (e.g., approximate volume) of the ith cavity. Notably, the term effective area is used to account for embodiments where a surface of the shared cavity wall is not entirely flat. The diffuse electromagnetic field power transmission coefficient of the electromagnetic wave(s) can be expressed as follows:

$$\langle \tau_{ij} \rangle = \frac{1}{4\pi^2} \int_{\varphi=0}^{2\pi} \int_{\theta=0}^{\pi/2} \int_{\alpha=0}^{2\pi} \tau(\theta, \varphi, \alpha) d\alpha\, d\theta \sin\theta d\varphi, \tag{4}$$

where $\tau(\theta,\varphi,\alpha)$ refers to an electric power transmission coefficient of the electromagnetic wave(s). The electric power transmission coefficient of the electromagnetic wave(s) can be expressed as a function of a wave amplitude transmission coefficient $T_A(\theta,\varphi,\alpha)$ of the electromagnetic wave(s) and as a wave angle transmission coefficient $T_\theta(\theta,\varphi,\alpha)$ of the electromagnetic wave(s) using the relation:

$$\tau(\theta, \varphi, \alpha) = \frac{c_j \cos(T_\theta(\theta, \varphi, \alpha))|T_A(\theta, \varphi, \alpha)|^2}{c_i \cos\theta}. \tag{5}$$

Similarly, using similar relationships, energy matrix module 112 can determine the loss factor $\beta_i$ from the ith cavity through the wall as:

$$\beta_i = \frac{c_i A_{ij} (\langle \tau_{ij} - r_{ij} \rangle)}{4\omega V_i}, \quad (6)$$

with:

$$\langle \tau_{ij} - r_{ij} \rangle = 1/4\pi^2 \int_{\varphi=0}^{2\pi} \int_{\theta=0}^{\pi/2} \int_{\alpha=0}^{2\pi} (\tau(\theta,\varphi,\alpha) - r(\theta,\varphi,\alpha)) \, d\alpha d\theta \sin\theta d\varphi \quad (7)$$

where $r(\theta,\varphi,\alpha)$ refers to the electric power transmission coefficient of the reflected electromagnetic wave(s). The electric power transmission coefficient of the reflected electromagnetic wave(s) can be determined from the wave amplitude reflection coefficient $R_A(\theta,\varphi,\alpha)$ using the relation:

$$r(\theta, \varphi, \alpha) = \frac{c_j \cos(R_\theta(\theta, \varphi, \alpha)) |R_A(\theta, \varphi, \alpha)|^2}{c_i \cos\theta}. \quad (8)$$

Figure 4:
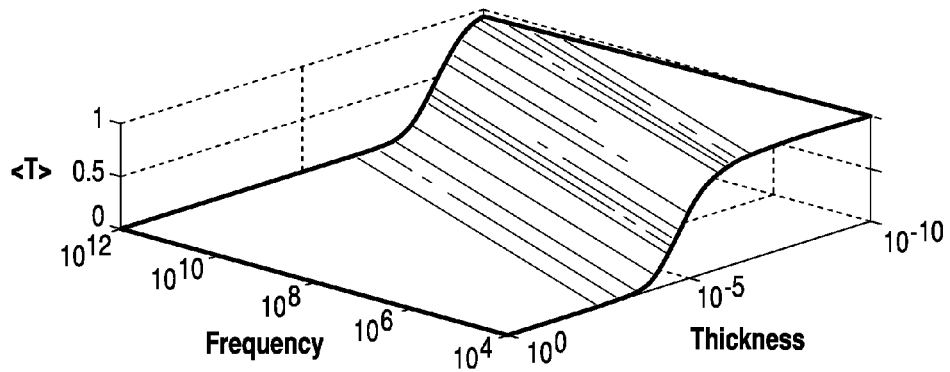
FIG. 4 illustrates a graphical representation of the evolution of a diffuse electromagnetic field power transmission of an electromagnetic wave coming in contact with a steel wall varying as a function of a frequency of the electromagnetic wave and a thickness of the steel wall.

Notably, calculating Equations (5) and (6) can require knowledge of the wave amplitude transmission coefficient $T_A(\theta,\varphi,\alpha)$ and the wave amplitude reflection coefficient $R_A(\theta,\varphi,\alpha)$ of the electromagnetic wave(s). In case of a shared cavity wall composed by a uniform layer of an isotropic material, the transmission and reflection law can be developed from Snell's law (also referred to as the Snell-Descartes law and the law of refraction). Snell's law is a formula describing the relationship between the angles of incidence and refraction, when referring to electromagnetic waves passing through a boundary between two different isotropic media. By way of example, FIG. 4 illustrates a graphical representation of the evolution of a diffuse electromagnetic field power transmission of an electromagnetic wave coming in contact with a steel wall varying as a function of a frequency of the electromagnetic wave in Hertz and a thickness of the steel wall in meters. Meanwhile, if the shared wall is not composed of a uniform layer of an isotropic material, Snell's law may not provide accurate measures of the wave amplitude transmission coefficient $T_A(\theta,\varphi,\alpha)$ and the wave amplitude reflection coefficient $R_A(\theta,\varphi,\alpha)$ of the electromagnetic wave(s). Accordingly, in these or other embodiments, the wave amplitude transmission coefficient $T_A(\theta,\varphi,\alpha)$ and the wave amplitude reflection coefficient $R_A(\theta,\varphi,\alpha)$ of the electromagnetic wave(s) can be determined experimentally. A non-patent reference Moon, K. S. & Choi, H. D. et al., *Dielectric Properties of Epoxy-Dielectrics-Carbon Black Composite for Phantom Materials at Radio Frequencies*, J. Appl. Polym. Sci., vol. 77, pp. 1294-1302 (2000) provides additional information related to non-isotropic materials, and is incorporated herein by reference.

Also, as with Equation (2), Equations (3) and (6) can be modified as necessary for the jth cavity by replacing a j subscript for each i subscript, and vice versa.

Moving now to the case of transmission of electromagnetic wave(s) through one or more aperture(s) in a perfectly conducting shared cavity wall, the coupling loss factor $\beta_{ij}$ from cavity i to cavity j can be determined by energy matrix module 112 by using either a wave approach or the diffuse-field reciprocity principle. The diffuse-field reciprocity principle provides that a loading applied (e.g., an induced electric field) by an electromagnetic wave field within a reverberant cavity on an electrical element can be expressed in terms of the energy in the electromagnetic wave field and the radiation properties of the electrical element (i.e., the way in which the electrical element would radiate into the reverberant cavity, were the reverberant cavity infinitely extended).

Using the wave approach, energy matrix module 112 can determine the coupling loss factor $\beta_{ij}$ from cavity i to cavity j differently depending on the nature (e.g., thickness) of the shared cavity wall and the nature (e.g., quantity) of the aperture(s). In any event, the shared cavity wall is assumed to be perfectly conducting.

First, addressing transmission of electromagnetic wave(s) through one arbitrarily shaped aperture of a thin shared cavity wall, the tangential electric and magnetic field on a surface S of the aperture can be described using generalized coordinates e and h. In some embodiments, a thin wall can refer to a shared cavity wall that is sufficiently thin that the thickness of the wall can be neglected. In specific embodiments, a thin wall can be sufficiently thin to neglect the thickness when the thickness is much less thick than a wavelength of the incident electromagnetic wave(s) (e.g., less than one tenth of the wavelength of the electromagnetic waves(s)). Accordingly, the electric power transmitted by surface S can be defined as:

$$P = \tfrac{1}{2} e^T h = \tfrac{1}{2} e^T Z_d e, \quad (9)$$

where $Z_d$ is the impedance matrix defined by impedance matrix $Z_{d,nm}$ such as:

$$\begin{pmatrix} -h_{n,y} \\ h_{n,x} \end{pmatrix} = Z_{d,nm} \begin{pmatrix} e_{n,x} \\ e_{n,y} \end{pmatrix}, \quad (10)$$

for w points at the surface S of the aperture, where:

$$Z_{d,nm} = \int\int_S \Gamma(\rho', \rho) u_n(\rho) u_m(\rho') d\rho d\rho' \quad (11)$$

and where $\Gamma(\rho',\rho)$ is the dyadic Green function defined as:

$$\Gamma(\rho', \rho) = \left( II_2 + \frac{1}{k^2} \nabla \nabla' \right) \frac{\exp(-jk|\rho' - \rho|)}{4\pi |\rho' - \rho|}. \quad (12)$$

Meanwhile, in a Fourier domain $Z_{d,nm}$ expressed as:

$$Z_{d,nm} = \int_{k_r=0}^{\infty} \tilde{\Gamma}_{nm}(k_r) U_n(k_r) U_m(k_r) dk_r \quad (13)$$

where $U_n(k_r)$ is the spectrum of the shape function $u_n(\rho)$ and $U_m(k_r)$ is the spectrum of the shape function $u_m(\rho)$ associated with the generalized coordinates of each point w of the surface. For example, the shape function $u_n(\rho)$ can be centered at a point on surface S with coordinates $x_n$ and taken to have a form:

$$u_n(r) = \frac{2J_1(k_s r)}{k_s r}. \quad (14)$$

where r is a distance of a general point on surface S from the point $x_n$. Therefore, the spectrum can be defined as:

$$U(k) = \begin{cases} 0, & k > k_s \\ 4\pi/k_s^2 & k \leq k_s \end{cases} \quad (15)$$

Meanwhile, integrating (e.g., analytically) over k from 0 to $k_s$, energy matrix module 112 can determine impedance matrix $Z_{d,nm}$. Having solved for impedance matrix $Z_{d,nm}$, energy matrix module 112 can then evaluate the electric power transmitted by surface S (e.g., using Equation (9)) and the electric power transmission coefficient $\tau(\theta,\varphi,\alpha)$ and the electric power reflection coefficient $r(\theta,\varphi,\alpha)$. These coefficients can be determined by combining the impedance matrices of the outer and inner surfaces of the aperture (e.g. both of which may be determined by Equation (13)) into a total impedance matrix. The electromagnetic field due to an incident electromagnetic wave of a specified heading and polarization can then be applied, and the resulting reflected and transmitted electromagnetic field(s) can be found by imposing the impedance relation. Having determined the reflected and transmitted electromagnetic field(s), the transmission and reflection coefficients can then be determined using Equation(s) (5) and (8). With this information, energy matrix module 112 can then proceed to calculate coupling loss factor $\beta_{ij}$ and loss factor $\beta_i$, such as, for example, using Equations (6) and (3), respectively. A non-patent reference A. Roberts, *Electromagnetic Theory of Diffraction by a Circular Aperture in a Thick, Perfectly Conducting Screen*, J. Opt. Soc. Am. A, vol. 4, No. 10 (October 1987) provides additional information related to electric power transmission through apertures, and is incorporated herein by reference.

Figure 5:
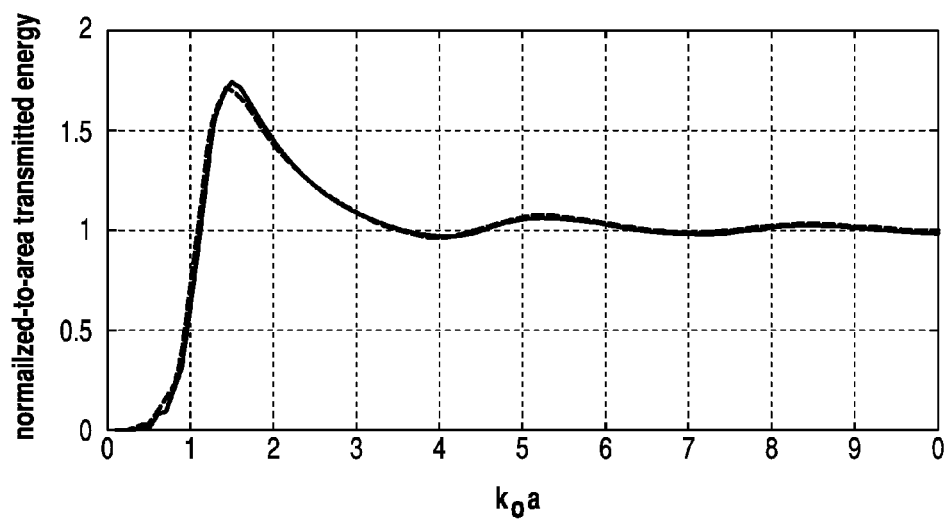
FIG. 5 illustrates a graphical diagram showing a normalized energy transfer through a circular aperture for a normal incident plane electromagnetic wave over various frequencies when calculated using a wave approach.

Briefly turning ahead in the drawings, FIG. 5 illustrates a graphical diagram showing a normalized energy transfer through a circular aperture of radius a for a normal incident plane electromagnetic wave over various frequencies $k_0$ when calculated using the foregoing wave approach (solid line) and according to an analytical solution (dashed line). Notably, the wave approach demonstrates very good agreement with the analytical solution.

Next, referring again back to FIG. 1, transmission of electromagnetic wave(s) through a periodic array of apertures in a shared cavity wall is addressed. The period array of apertures can be assumed to be an infinite array of identical apertures of arbitrary shape. For simplicity, it is assumed that the directors of periodicity of the period array of apertures correspond to the main directions x and y. Using the periodicity theory, energy matrix module 112 can solve in a Fourier domain the impedance matrix $Z_{d,nm}$ is:

$$Z_{d,nm} = \int_{-\infty}^{\infty} \int_{p,q=-\infty}^{+\infty} \delta\left(k_x - \gamma_x - \frac{p2\pi}{\Delta x}\right) \delta\left(k_y \gamma_y - \frac{q2\pi}{\Delta y}\right) \quad (16)$$

$$\frac{e^{i(k_x x + k_y y)}}{k_{0z}} \begin{bmatrix} 1 - \frac{k_x^2}{k^2} & -\frac{k_x k_y}{k^2} \\ -\frac{k_x k_y}{k^2} & 1 - \frac{k_y^2}{k^2} \end{bmatrix} U_n U_m dk_x dk_y$$

where $\Delta x$ and $\Delta y$ represent the size of the elementary cell of the array, and $\gamma_x$ and $\gamma_y$ represents the x and y components of the incident plane electromagnetic wave. The shape function $u_n(x,y)$ used by energy matrix module 112 to calculate Equation (16) to describe the tangential electric and magnetic field can be:

$$u_n(x, y) = \frac{\sin(k_s x)\sin(k_s y)}{k_s^2 xy}, \quad (17)$$

and the spectrum can be:

$$U(k) = \begin{cases} 0 & k_x > k_s \| k_y > k_s \\ 2/(\pi k_s^2) & k_x \leq k_s \, \& \, k_y \leq k_s \end{cases}. \quad (18)$$

As a result, energy matrix module 112 can solve impedance matrix $Z_{d,nm}$ as a finite sum over p and q of Equation (16). Energy matrix module 112 can then evaluate the electric power transmitted by surface S (e.g., using Equation (9)) and the electric power transmission coefficient $\tau(\theta,\varphi,\alpha)$ and the electric power reflection coefficient $\tau(\theta,\varphi,\alpha)$. These coefficients can be determined by combining the impedance matrices of the outer and inner surfaces of the aperture (e.g. both of which may be determined by Equation (13)) into a total impedance matrix. The electromagnetic field due to an incident electromagnetic wave of a specified heading and polarization can then be applied, and the resulting reflected and transmitted electromagnetic field(s) can be found by imposing the impedance relation. Having determined the reflected and transmitted electromagnetic field(s), the transmission and reflection coefficients can then be determined using Equation(s) (5) and (8). With this information, energy matrix module 112 can then proceed to calculate coupling loss factor $\beta_{ij}$ and loss factor $\beta_i$, such as, for example, using Equations (6) and (3), respectively.

Finally, addressing transmission of electromagnetic wave(s) through one arbitrarily shaped aperture of a thick shared cavity wall, when the thickness of the shared cavity wall is sufficiently large that it cannot be neglected without resulting in an unacceptable lack of accuracy, energy matrix module 112 can determine coupling loss factor $\beta_{ij}$ and loss factor $\beta_i$ using a combination approach addressing transmission of electromagnetic wave(s) through thin walls and propagation of electromagnetic wave(s) inside a wave guide.

Figure 6:
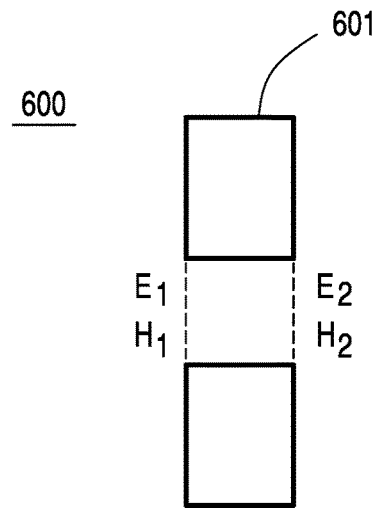
FIG. 6 illustrates a representative block diagram of a thick shared cavity wall of an electrical system, according to an embodiment.
Figure 7:
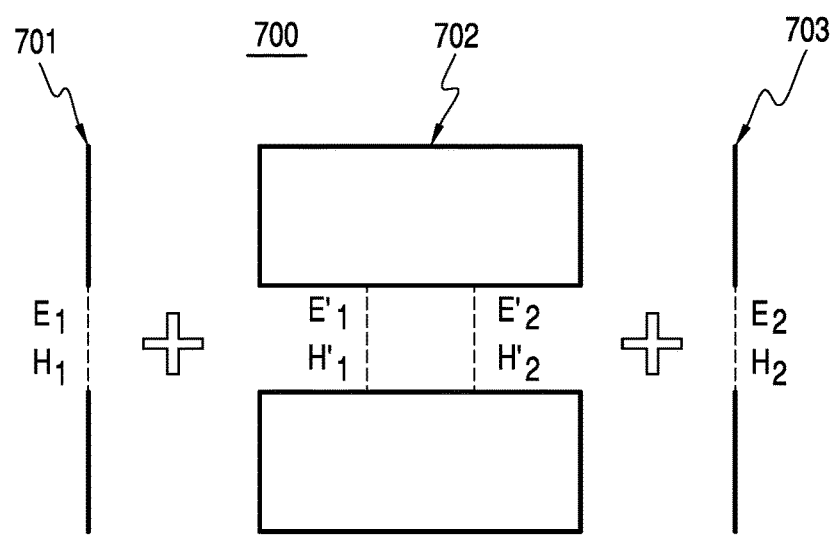
FIG. 7 illustrates a representative block diagram of a first thin shared cavity wall, a wave guide, and a second thin shared cavity wall of an electrical system representative of the electrical system of FIG. 6, according to an embodiment.

Turning ahead again in the drawings, FIGS. 6 & 7 illustrate the decomposition approach of representing a thick wall as two thin walls and a wave guide. Specifically, FIG. 6 illustrates a representative block diagram of a thick shared cavity wall 601 of an electrical system 600, according to an embodiment. Meanwhile, FIG. 7 illustrates a representative block diagram of a first thin shared cavity wall 701, a wave guide 702, and a second thin shared cavity wall 703 of an electrical system 700, according to an embodiment. Electrical system 700 can be similar or identical to electrical system 600 (FIG. 6). Meanwhile, electrical system 600 (FIG. 6) and electrical system 700 each can be similar or identical to electrical system 200 (FIG. 2). Equation (19) as follows can correspond to thick shared cavity wall 601 (FIG. 6) of electrical system 600 (FIG. 6) while Equations (20) through (22) as follow can correspond to first thin shared cavity wall 701, wave guide 702, and second thin shared cavity wall 703 of electrical system 700, respectively:

$$\begin{pmatrix} E_i \\ E_j \end{pmatrix} = Z_t \begin{pmatrix} H_i \\ H_j \end{pmatrix} \quad (19)$$

$$E_i = Z_{di} H_i \quad (20)$$

-continued $$\begin{pmatrix} E'_i \\ E'_j \end{pmatrix} = Z_c \begin{pmatrix} H'_i \\ H'_j \end{pmatrix} \quad (21)$$

$$E_j = Z_{dj} H_j. \quad (22)$$

Now returning again to FIG. 1, the impedance matrix $Z_c$ is the impedance matrix relating to the electric and magnetic fields on the face(s) of the cavity formed by the aperture through the thick shared cavity wall (e.g., corresponding to wave guide 702 (FIG. 7)). Impedance matrix $Z_c$ can be calculated by energy matrix module 112, for example, by using a finite element method. The impedance matrix $Z_{di}$ is the impedance matrix relating to the thick shared cavity wall at the ith cavity (e.g., corresponding to thin wall 701 (FIG. 7)) and the impedance matrix $Z_{dj}$ is the impedance matrix of the thick shared cavity wall corresponding to the jth cavity (e.g., corresponding to thin wall 702 (FIG. 7)) for electromagnetic radiation into a semi-infinite space. Both impedance matrix $Z_{di}$ and $Z_{dj}$ can be determined by energy matrix module 112 using Equation (13) for a single arbitrary aperture and using Equation (16) for period apertures. The impedance matrix $Z_t$ is the impedance matrix provided when the aperture cavity is coupled to the two semi-infinite domains, and it can be expressed in terms of $Z_c$, $Z_{di}$, and $Z_{dj}$.

After solving for impedance matrices $Z_{di}$, $Z_{dj}$, and $Z_c$, energy matrix module 112 can evaluate the electric power transmitted by surface S of the aperture (e.g., modifying Equation (9) to replace $Z_d$ with $Z_t$), the electric power transmission coefficient $\tau(\theta,\varphi,\alpha)$, and the electric power reflection coefficient $\tau(\theta,\varphi,\alpha)$. These coefficients can be determined, as similarly explained above for thin walls and periodic apertures, by applying the electromagnetic field due to an incident electromagnetic wave of a specified heading, and imposing the impedance relation of Equation (19) to determine the resulting reflected and transmitted electromagnetic field(s). Having determined the reflected and transmitted electromagnetic field(s), the transmission and reflection coefficients can then be determined using Equation(s) (5) and (8). With this information, energy matrix module 112 can then proceed to calculate coupling loss factor $\beta_{ij}$ and loss factor $\beta_i$, such as, for example, using Equations (6) and (3), respectively.

Meanwhile, as stated previously, in some embodiments, the coupling loss factor $\beta_{ij}$ from cavity i to cavity j also can be determined by energy matrix module 112 by applying the diffuse-field reciprocity principle. Specifically, excluding the example of a periodic array of apertures, energy matrix module 112 can solve for the coupling loss factor $\beta_{ij}$ using Equation (23) as follows:

$$\omega n_i \beta_{ij} = \left(\frac{2}{\pi}\right) Tr[Z_d^H Z_t^{-1} Z_d^H Z_t^{-T*}], \quad (23)$$

where the impedance matrix $Z_t$ is defined by:

$$Z_t = Z_c - \begin{pmatrix} Z_{di} & 0 \\ 0 & Z_{dj} \end{pmatrix}_{Zt=Zc-Zdi00Zd2}, \quad (24)$$

and $Z_d^H$ represents the Hermitian part of the matrix $Z_d$. For Equation (24), as for Equation (21) above, impedance matrix $Z_c$ is the impedance matrix relating to the electric and magnetic fields on the face(s) of the cavity formed by the aperture through the thick shared cavity wall (e.g., corresponding to wave guide 702 (FIG. 7)). Accordingly, impedance matrix $Z_c$ can again be calculated by energy matrix module 112, for example, by using a finite element method. A non-patent reference C. Huang & R. Kodis et al., *Diffraction by Apertures*, Journal of Applied Physics, vol. 26, No. 2 (February 1955) provides additional information related to electric power transmission through apertures, and is incorporated herein by reference.

As noted again, the approach taken in determining the coupling loss factors and/or loss factors determined by using Equations (8) through (24) can also be applied to the jth cavity by replacing a j subscript, when applicable, for each i subscript, and vice versa.

After determining the loss factors of the one or more first cavities and the one or more second cavities, the coupling loss factors of the one or more first cavities and the one or more second cavities, the cavity modal densities of the one or more first cavities and the one or more second cavities can be used to calculate the energy matrix in Equation (1) and/or Equation (39).

Using the energy matrix determined by energy matrix module 112, mean energy module 113 can determine (e.g., calculate) a mean energy of the electromagnetic field(s) in the one or more first cavities and one or more second cavities of the electrical system. That is, for the illustrative purposes of the simplified embodiment introduced with respect to Equation (1), mean energy module 113 can determine (e.g., calculate) a mean energy of the electromagnetic field(s) in the one cavity of the one or more first cavities and the one cavity of the one or more second cavities of the electrical system. Notably, the statistical mean of the electromagnetic energy $E_i$ in the ith cavity (e.g., the one cavity of the one or more first cavities) at frequency $\alpha$ can be written in terms of the magnetic field H in the form:

$$E_i = (\tfrac{1}{2}) \mu_i V_i E[HH], \quad (25)$$

where $\mu_i$ and $V_i$ are the permeability and the volume (e.g., approximate volume) of the ith cavity, respectively. The symbol E[ ] represents the statistical expectation (i.e., the ensemble mean) of the field(s), corresponding to an average taken over an ensemble of random realizations of the ith cavity. At large statistical overlap, this value does not depend on the location of the electromagnetic field(s) within the cavity, and hence the spatial point at which the magnetic field H is evaluated does not need to be specified in Equation (25).

Meanwhile, for reverberant fields at high statistical overlap, the ensemble average energy flow between the ith cavity (e.g., the one cavity of the one or more first cavities of the electrical system) and the jth cavity (e.g., the one cavity of the one or more second cavities of the electrical system) can be expressed in the form:

$$P_{ij} = \omega \beta_{ij} n_i \left(\frac{E_i}{n_i} - \frac{E_j}{n_j}\right). \quad (26)$$

The discussion of energy matrix module 112 provides for calculating the coupling loss factor $\beta_{ij}$, cavity modal density $n_i$, and cavity modal density $n_j$. Notably, reciprocity provides the following relationship between the coupling loss factors $\beta_{ij}$ and $\beta_{ji}$, cavity modal density $n_i$, and cavity modal density $n_j$:

$$\beta_{ij} n_i = \beta_{ji} n_j. \quad (27)$$

Meanwhile, the ensemble mean of the electric power loss in the ith cavity due to wall losses and other dissipative effects can be written as:

$$P_{i,diss} = \omega \beta_i E_i, \quad (28)$$

and a power balance equation for the ith cavity can be provided by noting that the ensemble mean of the electric power dissipated by the ith cavity $P_{i,diss}$ plus the ensemble mean of the net electric power transferred between the ith cavity and the jth cavity $P_{ij}$ is balanced by the ensemble mean of the electric power input into the ith cavity from the electromagnetic wave creation element(s) $P_{i,in}$ so that:

$$P_{i,diss} + P_{ij} = P_{i,in} \quad (29)$$

Applying the relationships of Equations (26) through (29) for both the ith and jth cavity yields the relationship:

$$\begin{pmatrix} \omega \beta_i n_i + \omega \beta_{ij} n_i & -\omega \beta_{ij} n_i \\ -\omega \beta_{ji} n_j & \omega \beta_j n_j + \omega \beta_{ji} n_j \end{pmatrix} \begin{pmatrix} E_i/n_i \\ E_j/n_j \end{pmatrix} = \begin{pmatrix} P_{i,in} \\ P_{j,in} \end{pmatrix}. \quad (30)$$

Notably, the ensemble mean of the electric power input into the ith cavity from the electromagnetic wave creation element(s) $P_{i,in}$ can be equal to the electric power radiated into an unbounded space by the electromagnetic wave creation element(s) at the ith cavity. Mean energy module 113 can readily determine the electric power radiated into an unbounded space of the electromagnetic wave creation element(s) at the ith cavity given the details of the electromagnetic wave creation element(s) at the ith cavity by using antenna theory or can be provided the electric power radiated into an unbounded space of the electromagnetic wave creation element(s) at the ith cavity by a user of apparatus 100 as an input to mean energy module 113. Likewise, the ensemble mean of the electric power input into the jth cavity from the electromagnetic wave creation element(s) $P_{j,in}$ can be equal to the electric power radiated into an unbounded space by the electromagnetic wave creation element(s) at the jth cavity, which can be determined in a similar manner as provided for the ensemble mean of the electric power input into the ith cavity from the electromagnetic wave creation element(s) $P_{i,in}$. As a result, mean energy module 113 can determine the right side of Equation (30). Meanwhile, using the energy matrix of Equation (1) determined by the energy matrix module 112 as discussed above at the left hand side of Equation (30), mean energy module 113 can solve Equation (30) to determine (e.g., calculate) the ensemble averaged energy $E_i$ of the ith cavity (e.g., the one cavity of the one or more first cavities of the electrical system) and the ensemble averaged energy $E_j$ of the jth cavity (e.g., the one cavity of the one or more second cavities of the electrical system). With ensemble averaged energy $E_i$ and ensemble averaged energy $E_j$ determined, mean energy module 113 can proceed to determine (e.g., calculate) the electromagnetic field(s) in the ith cavity (e.g., the one cavity of the one or more first cavities of the electrical system) and the jth cavity (e.g., the one cavity of the one or more second cavities of the electrical system) by implementing Equation (25).

Further, using the energy matrix determined by energy matrix module 112, energy variance module 114 can determine (e.g., calculate) an energy variance of the electromagnetic field(s) in the one or more first cavities and one or more second cavities of the electrical system. That is, for the illustrative purposes of the simplified embodiment introduced with respect to Equation (1), energy variance module 114 can determine (e.g., calculate) an energy variance of the electromagnetic field(s) in the one cavity of the one or more first cavities and the one cavity of the one or more second cavities of the electrical system.

Generally, the ensemble variance of the ith cavity (e.g., the one cavity of the one or more first cavities of the electrical system) and the ensemble variance of the jth cavity (e.g., the one cavity of the one or more second cavities of the electrical system) can be determined by applying universal statistical results relating to the occurrence of the Gaussian orthogonal ensemble (GOE) in random matrix theory. At high statistical overlap, the statistics of the natural frequencies and mode shapes of the ith cavity (e.g., the one cavity of the one or more first cavities of the electrical system) and the ensemble variance of the jth cavity (e.g., the one cavity of the one or more second cavities of the electrical system) are governed by the GOE, and it is possible to predict the variance of each cavity response without knowing the precise details of the random variations in the cavity properties. Applying the foregoing approach yields:

$$\text{Var}[\bar{E}_i] = \sum_{j=1}^{2} (D_{0,ij}^{-1})^2 \text{Var}[P_{j,in}] + \sum_{j=1}^{2} \sum_{s \neq j} \left[ (D_{0,ij}^{-1} - D_{0,is}^{-1}) \hat{E}_S \right]^2 \text{Var}[D_{ran,is}], \quad (31)$$

where $D_{0,ij}^{-1}$ is the ijth entry of the inverse matrix of Equation (1) and where the ensemble energy $E_S$ is the ensemble averaged energy $E_i$ of the ith cavity (e.g., the one cavity of the one or more first cavities of the electrical system) as provided by Equation (30) above and $n_s$ refers to the modal cavity density of the ith cavity to satisfy the following relationship of Equation (31):

$$\hat{E}_s = E_s/n_s. \quad (32)$$

The other terms that appear in Equation (32) are given by:

$$\text{Var}[P_{j,in}] = P_{j,in}^2 r^2 (\alpha_j, m'_j, B'_j), \text{Var}[D_{ran,js}] D_{0,js}^2 r^2 (\alpha_{js}, m'_j, B'_j) \quad (33, 34)$$

where, for cavity j, $m'_j$ refers to the effective modal overlap factor, which can be expressed in terms of the electrical system loss factors, coupling loss factors, and modal densities via:

$$m'_j = \frac{1}{D_{jj}^{-1}}, \quad (35)$$

$\alpha_j$ and $\alpha_{js}$ are loading factors that are governed respectively by the nature of the electric power input and the geometry of the electrical system coupling. For example, loading factor $\alpha_j$ can be determined by considering the generalized excitation acting on an eigen-mode of the jth cavity due to the electric power input. Loading factor $\alpha_j$ can be defined as the fourth power of the modulus of the generalized excitation, divided by the square of the second power of the modulus of the generalized excitation. If the excitation is deterministic, then the loading factor is governed by the statistics of the jth cavity eigen-modes. These modes are Gaussian under the GOE approximation, and the resulting factor can be 3. Meanwhile, loading factor $\alpha_{js}$ can be determined, similarly, but arises from the electromagnetic field in the jth cavity, which is complex Gaussian. For small apertures, loading factor $\alpha_{js}$ can be 6. The value of loading factors $\alpha_j$ and $\alpha_{js}$ can vary with the nature of the loading on the electrical system, but in many embodiments, can be calculated by considering the statistics of the generalized excitations. Further, the bandwidth parameter $B'_j$ satisfies the expression of:

$$B'_j = \Delta/(\omega \beta_j) \tag{36}$$

and applies only when the concern is with the variance of energies which have been averaged over a frequency band $\Delta$. For the narrow band case (i.e., $\Delta=0$), the function r that appears in Equations (33) and (34) has the form:

$$r^2(\alpha, m, 0) = \frac{1}{\pi m}\left\{\alpha - 1 + \frac{1}{2\pi m}[1 - \exp(-2\pi m)] + E_1(\pi m)\left[\cosh(\pi m) - \frac{1}{\pi m}\sinh(\pi m)\right]\right\}, \tag{37}$$

where $E_1$ is the exponential integral and for an averaged band case, the function r that appears in Equations (33) and (34) has the form:

$$r^2(\alpha, m, B) = \tag{38}$$

$$\frac{\alpha - 1}{\pi m}\left(\frac{1}{B^2}\right)\left\{2B\left[\frac{\pi}{2} - \tan^{-1}\left(\frac{1}{B}\right)\right] - \ln(1 + B^2)\right\} + \left(\frac{1}{\pi m B}\right)^2 \ln(1 + B^2).$$

Energy variance module 114 can use loading factors $\alpha_j$ and $\alpha_{js}$, loss factor $\beta_j$, effective modal overlap factor $m'_j$, and bandwidth parameter $B'_j$ to determine the ensemble variance of the ith cavity (e.g., the one cavity of the one or more first cavities of the electrical system). Energy variance module 114 can determine the ensemble variance of the jth cavity (e.g., the one cavity of the one or more second cavities of the electrical system) using a comparable approach.

Having explained the functionality of energy matrix module 112, mean energy module 113, and energy variance module 114 primarily with respect to the one cavity of the one or more first cavities and the one cavity of the one or more second cavities of the electrical system, as provided above, energy matrix module 112, mean energy module 113, and energy variance module 114 can perform their respective functions for an electrical system comprising 1 to N cavities coupled together with any suitable coupling arrangements by modification of Equations (1), (25), and (31). Specifically, Equation (39) expands the energy matrix of Equation (1) and can be provided as follows:

$$\begin{pmatrix} \omega\beta_1 n_1 + \omega\sum_{j\neq 1}\beta_{1j}n_1 & -\omega\beta_{12}n_1 & \cdots & -\omega\beta_{1N}n_1 \\ -\omega\beta_{21}n_2 & \omega\beta_2 n_2 + \omega\sum_{j\neq 2}\beta_{2j}n_2 & \cdots & -\omega\beta_{2N}n_2 \\ \vdots & \vdots & \ddots & \\ -\omega\beta_{N1}n_N & -\omega\beta_{N2}n_N & & \omega\beta_N n_N + \omega\sum_{j\neq N}\beta_{Nj}n_N \end{pmatrix}. \tag{39}$$

Further, Equation (40) expands the mean energy calculation of Equation (25) and can be provided as follows:

$$\begin{pmatrix} \omega\beta_1 n_1 + \omega\sum_{j\neq 1}\beta_{1j}n_1 & -\omega\beta_{12}n_1 & \cdots & -\omega\beta_{1N}n_1 \\ -\omega\beta_{21}n_2 & \omega\beta_2 n_2 + \omega\sum_{j\neq 2}\beta_{2j}n_2 & \cdots & -\omega\beta_{2N}n_2 \\ \vdots & \vdots & \ddots & \\ -\omega\beta_{N1}n_N & -\omega\beta_{N2}n_N & & \omega\beta_N n_N + \omega\sum_{j\neq N}\beta_{Nj}n_N \end{pmatrix} \tag{40}$$

$$\begin{pmatrix} E_1/n_1 \\ E_2/n_2 \\ \vdots \\ E_N/n_N \end{pmatrix} = \begin{pmatrix} P_{1,in} \\ P_{2,in} \\ \vdots \\ P_{N,in} \end{pmatrix}.$$

Finally, Equation (41) expands the energy variance calculation of Equation (31) and can be provided as follows:

$$\text{Var}[\bar{E}_i] = \tag{41}$$

$$\sum_{j=1}^{N}(D_{0,ij}^{-1})^2 \text{Var}[P_{j,in}] + \sum_{j=1}^{N}\sum_{s\neq j}\left[(D_{0,ij}^{-1} - D_{0,is}^{-1})\hat{E}_S\right]^2 \text{Var}[D_{ran,ks}].$$

Circling back now to measurement module 110 and electrical parameters module 111, given the foregoing context of the functionality of energy matrix module 112, mean energy module 113, and energy variance module 114 as discussed above, measurement module 110 and electrical parameters module 111 can receive physical information about the electrical system from which energy matrix module 112, mean energy module 113, and energy variance module 114 can perform the above described functionality. Notably, the functionality of energy matrix module 112, mean energy module 113, and energy variance module 114 can be repeated for varying electrical parameter(s) of the electromagnetic wave creation element(s) of the electrical system provided by electrical parameters module 111 (i.e., multiple electric power levels, multiple electric frequencies, multiple wave lengths, etc. of the electric waves emitted by the electromagnetic wave creation element(s)).

Meanwhile, modification module 115 can be operable to use the mean energy of the one or more electromagnetic fields in the one or more first cavities and the one or more second cavities of the electrical system (e.g., as determined by mean energy module 113) and the energy variance of the one or more electromagnetic fields in the one or more first cavities and the one or more second cavities of the electrical system (e.g., as determined by energy variance module 114) to determine one or more potential changes to at least one of (i) the one or more first cavities of the electrical system, (ii) the one or more second cavities of the electrical system, or (iii) the at least one electromagnetic wave creation element(s) of the electrical system. These changes can be intended to mitigate or eliminate induced electric current in the electrical system to prevent damage to the electrical system and/or to prevent electrical interference with the electrical system. In other words, modification module 115 can be configured to indicate to a user of apparatus 100 how the electrical system could be reconfigured to prevent damage to the electrical system and/or to prevent electrical interference with the electrical system. Meanwhile, given these indications, the user can apply one or more of the potential changes, as desirable.

For example, exemplary changes can comprise adding electromagnetic shielding to one or more electrical components located in the one or more first cavities and/or the one or more second cavities of the electrical system. Further exemplary changes can comprise moving the electrical component(s) and/or if possible, moving one or more wall or cavity surfaces of the electrical system.

In many embodiments, in order to determine these changes, modification module 115 can be configured to model the electromagnetic field(s) in the one or more first cavities and the one or more second cavities of the electrical system based upon the mean energy of the electromagnetic field(s) in the one or more first cavities and the one or more second cavities of the electrical system (e.g., at each frequency) and the energy variance of the electromagnetic field(s) in the one or more first cavities and the one or more second cavities of the electrical system (e.g., at each frequency). In some examples, the mean energy of the electromagnetic field(s) the energy variance of the electromagnetic field(s) in the cavities can be determined with a log normal distribution and/or plotted on a graph for various frequencies. Meanwhile, after modeling the electromagnetic field(s), modification module 115 can determine confidence bands of a maximum energy of the electromagnetic field(s) in the one or more first cavities and the one or more second cavities of the electrical system. These confidence bands can be determined using Equation (31) and/or (39). Then, modification module 115 can determine a probability that the maximum energy of the electromagnetic field(s) in the electromagnetic field(s) in the one or more first cavities and the one or more second cavities of the electrical system is equal to or greater than a predetermined energy level. When the probability that the maximum energy of the electromagnetic field(s) the electromagnetic field(s) in the one or more first cavities and the one or more second cavities of the electrical system is equal to or greater than the predetermined energy level is larger than a predetermine probability value, the modification module 115 can indicate changes to the electrical system that will lower the probability that the maximum energy of the electromagnetic field(s) the electromagnetic field(s) in the one or more first cavities and the one or more second cavities of the electrical system is equal to or greater than the predetermined energy level. In some embodiments, part of determining these changes can be implemented by simulating (e.g., iteratively) other configurations of the electrical system and comparing the configurations. In many embodiments, although the predetermined probability value can depend on the acceptable level of risk of damage and/or interference with the electrical system, in specific examples, the predetermined probability value can be approximately 1, 3, 5, 10, 20 or 50 percent.

Some embodiments also include a method of providing an apparatus. The apparatus can be similar or identical to apparatus 100 (FIG. 1). Accordingly, the method can comprise one or more activities of providing one or more modules of the apparatus, wherein the module(s) can be similar or identical to the module(s) of apparatus 100 (FIG. 1) as described above.

Figure 8:
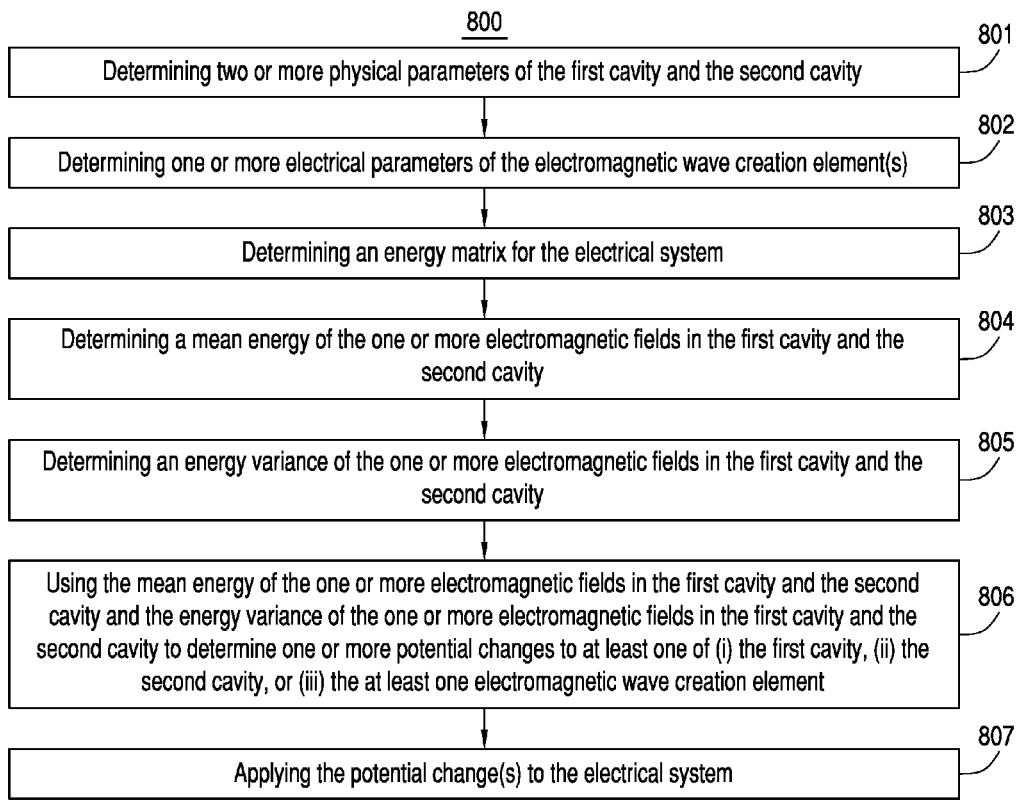
FIG. 8 illustrates a flow chart for an embodiment of a method of determining one or more electromagnetic fields in a first cavity coupled to a second cavity of an electrical system.

Turning ahead now in the drawings, FIG. 8 illustrates a flow chart for an embodiment of a method 800 of determining one or more electromagnetic fields in a first cavity coupled to a second cavity. The electromagnetic field(s) can be caused by one or more electrical waves emitted by at least one electromagnetic wave creation element of the electrical system. Method 800 is merely exemplary and is not limited to the embodiments presented herein. Method 800 can be employed in many different embodiments or examples not specifically depicted or described herein. In some embodiments, the activities, the procedures, and/or the processes of method 800 can be performed in the order presented. In other embodiments, the activities, the procedures, and/or the processes of method 800 can be performed in any other suitable order. In still other embodiments, one or more of the activities, the procedures, and/or the processes in method 800 can be combined or skipped.

In some embodiments, the first cavity can be similar to one cavity of the one or more first cavities described above with respect to apparatus 100 (FIG. 1) and/or similar or identical to one cavity of one or more first cavities 201 (e.g., cavity 205); and/or the second cavity can be similar to one cavity of the one or more second cavities described above with respect to apparatus 100 (FIG. 1) and/or similar or identical to one cavity of one or more second cavities 202 (e.g., cavity 206). In these or other embodiments, the electrical system can be similar or identical to the electrical system described above with respect to apparatus 100 (FIG. 1) and/or similar or identical to electrical system 200 (FIG. 2). Further in these or in other embodiments, the electromagnetic wave creation element(s) can be similar or identical to the electromagnetic wave creation element(s) described above with respect to apparatus 100 (FIG. 1) and/or similar or identical to electromagnetic wave creation element(s) 203 (FIG. 2).

Figure 9:
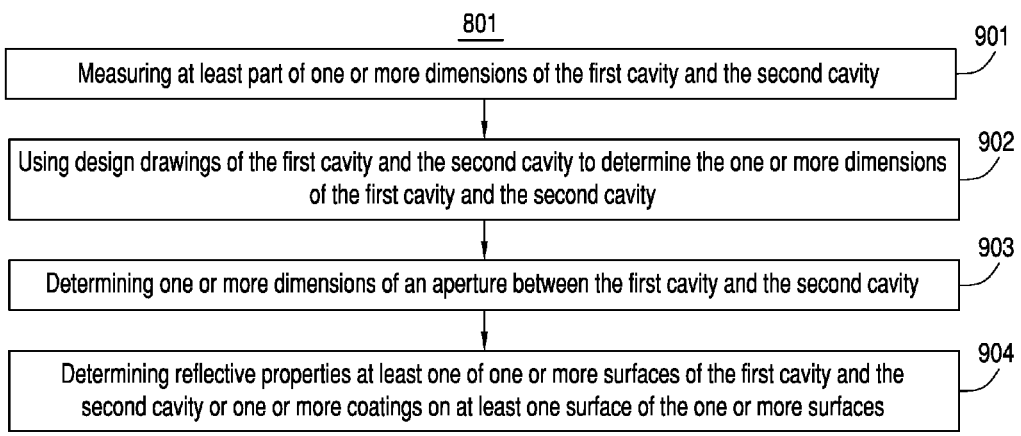
FIG. 9 illustrates an exemplary activity of determining two or more physical parameters of the first cavity and the second cavity of the electrical system, according to the embodiment of FIG. 8.

In many embodiments, method 800 can comprise activity 801 of determining two or more physical parameters of the first cavity and the second cavity. In many embodiments, the physical parameter(s) of the first cavity and the second cavity can be similar or identical to the physical parameter(s) of the one or more first cavities and the one or more second cavities described above with respect to apparatus 100 (FIG. 1). FIG. 9 illustrates an exemplary activity 801, according to the embodiment of FIG. 8.

For example, activity 801 can comprise activity 901 of measuring at least part of one or more dimensions of the first cavity and the second cavity.

Further, activity 801 can comprise activity 902 of using design drawings of the first cavity and the second cavity to determine the one or more dimensions of the first cavity and the second cavity.

Further still, activity 801 can comprise activity 903 of determining one or more dimensions of an aperture between the first cavity and the second cavity. In some embodiments, the aperture can be similar or identical to the aperture(s) described above with respect to apparatus 100 (FIG. 1) and/or aperture 204 (FIG. 2).

Even further still, activity 801 can comprise activity 904 of determining reflective properties at least one of one or more surfaces of the first cavity and the second cavity or one or more coatings on at least one surface of the one or more surfaces. In some embodiments, the surface(s) and/or coating(s) can be similar or identical to the surface(s) and/or coating(s) described above with respect to electrical system 200 (FIG. 2).

Turning now back to FIG. 8, method 800 can comprise activity 802 of determining one or more electrical parameters of the electromagnetic wave creation element(s). In some embodiments, performing activity 802 can comprise (i) determining an electric power of one or more frequencies of the electromagnetic wave(s) emitted by the electromagnetic wave creation element(s), (ii) determining at least one frequency of interest from the one or more frequencies of the electromagnetic wave(s) emitted by the electromagnetic wave creation element(s), and/or (iii) determining at least one wave length of the electromagnetic wave(s) emitted by the electromagnetic wave creation element(s).

Figure 10:
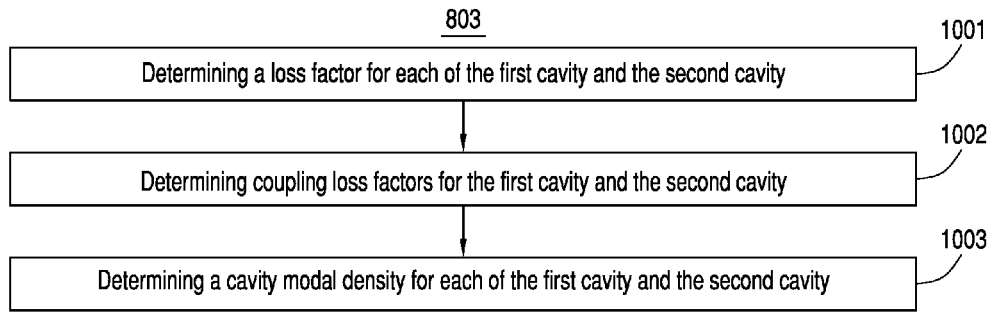
FIG. 10 illustrates an exemplary activity of determining an energy matrix for the electrical system, according to the embodiment of FIG. 8.

Further, method 800 can comprise activity 803 of determining an energy matrix for the electrical system. In some embodiments, performing activity 803 can be similar or identical to determining the energy matrix for the electrical system as described above with respect to apparatus 100 (FIG. 1). FIG. 10 illustrates an exemplary activity 803, according to the embodiment of FIG. 8.

For example, activity 803 can comprise activity 1001 of determining a loss factor for each of the first cavity and the second cavity; activity 1002 of determining coupling loss factors for the first cavity and the second cavity; and/or activity 1003 of determining a cavity modal density for each of the first cavity and the second cavity. Performing activity 1001 can be similar or identical to determining a coupling factor for each of the first cavity and the second cavity as described above with respect to apparatus 100 (FIG. 1). Further, performing activity 1002 can be similar or identical to determining coupling loss factors for the first cavity and the second cavity as described above with respect to apparatus 100 (FIG. 1). Further still, performing activity 1003 can be similar or identical to determining a cavity modal density for each of the first cavity and the second cavity as described above with respect to apparatus 100 (FIG. 1).

Turning again to FIG. 8, method 800 can comprise activity 804 of determining a mean energy of the one or more electromagnetic fields in the first cavity and the second cavity. In many embodiments, performing activity 804 can be similar or identical to determining a mean energy of the one or more electromagnetic fields in the one or more first cavities and the one or more second cavities as described above with respect to apparatus 100 (FIG. 1). For example, in some embodiments, performing activity 805 can comprise inverting the energy matrix to determine the mean energy of the one or more electromagnetic fields in the first cavity and the second cavity.

Figure 11:
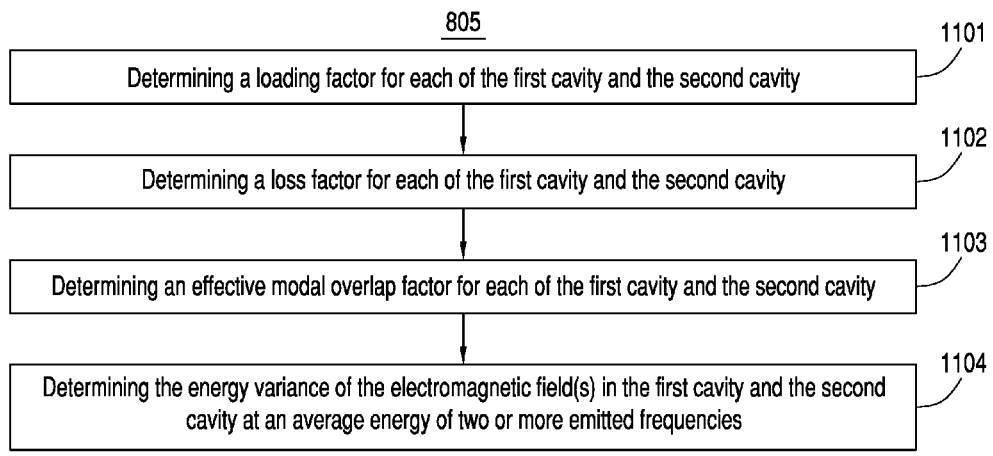
FIG. 11 illustrates an exemplary activity of determining an energy variance of the electromagnetic field(s) in the first cavity and the second cavity of the electrical system, according to the embodiment of FIG. 8.

Further, method 800 can comprise activity 805 of determining an energy variance of the one or more electromagnetic fields in the first cavity and the second cavity. In some embodiments, performing activity 805 can be similar or identical to determining an energy variance of the one or more electromagnetic fields in the one or more first cavities and the one or more second cavities as described above with respect to apparatus 100 (FIG. 1). FIG. 11 illustrates an exemplary activity 805, according to the embodiment of FIG. 8.

For example, activity 805 can comprise an activity 1101 of determining a loading factor for each of the first cavity and the second cavity. In some embodiments, performing activity 1101 can be similar or identical to determining the loading factor for each of the first cavity and the second cavity as described above with respect to apparatus 100 (FIG. 1).

In many embodiments, activity 805 can comprise an activity 1102 of determining a loss factor for each of the first cavity and the second cavity. In these or other embodiments, performing activity 1102 can be similar or identical to determining the loss factor for each of the first cavity and the second cavity as described above with respect to apparatus 100 (FIG. 1).

In many embodiments, activity 805 can comprise an activity 1103 of determining an effective modal overlap factor for each of the first cavity and the second cavity. In these or other embodiments, performing activity 1103 can be similar or identical to determining the effective modal overlap factor for each of the first cavity and the second cavity as described above with respect to apparatus 100 (FIG. 1).

In some embodiments, activity 805 can comprise an activity 1104 of determining the energy variance of the electromagnetic field(s) in the first cavity and the second cavity at an average energy of two or more emitted frequencies. In these or other embodiments, performing activity 1104 can be similar or identical to determining the energy variance of the electromagnetic field(s) in the first cavity and the second cavity at the average energy of two or more emitted frequencies as described above with respect to apparatus 100 (FIG. 1). In some embodiments, activity 1104 can be omitted.

Returning once again to FIG. 1, in many embodiments, method 800 can comprise activity 806 of using the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element. Notably, in many embodiments, activity 806 can be performed after one or more of activities 801-805. Further, the potential change(s) can be similar or identical to the potential change(s) discussed above with respect to apparatus 100 (FIG. 1).

Figure 12:
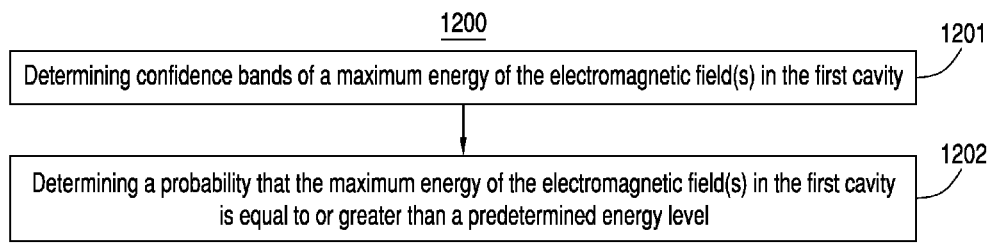
FIG. 12 illustrates an exemplary activity of determining a model of one or more electromagnetic fields in a first cavity based upon (i) a mean energy of the one or more electromagnetic fields in the first cavity and the second cavity and (ii) an energy variance of one or more electromagnetic fields in the first cavity and the second cavity, according to an embodiment.

In some embodiments, performing activity 806 can comprise determining a model of the one or more electromagnetic fields in the first cavity based upon (i) the mean energy of the one or more electromagnetic fields in the first cavity and the second cavity and (ii) the energy variance of the one or more electromagnetic fields in the first cavity and the second cavity. FIG. 12 illustrates an exemplary activity 1200 of determining a model of the one or more electromagnetic fields in the first cavity based upon (i) the mean energy of the one or more electromagnetic fields in the first cavity and the second cavity and (ii) the energy variance of the one or more electromagnetic fields in the first cavity and the second cavity, according to an embodiment.

For example, activity 1200 can comprise activity 1201 of determining confidence bands of a maximum energy of the electromagnetic field(s) in the first cavity. Further, activity 1200 can comprise activity 1202 of determining a probability that the maximum energy of the electromagnetic field(s) in the first cavity is equal to or greater than a predetermined energy level. When the probability that the maximum energy of the one or more electromagnetic fields in the first cavity is equal to or greater than the predetermined energy level is larger than a predetermine value, activity 807 (FIG. 8) can be performed.

Turning back to FIG. 8, method 800 can comprise activity 807 of applying the potential change(s) to the electrical system. In many embodiments, activity 807 can be performed after activity 806.

In many embodiments, at least part of activity 801, activity 802, activity 803, activity 804, activity 805, activity 806, activity 901, activity 902, activity 903, activity 904, activity 1001, activity 1002, activity 1003, activity 1101, activity 1102, activity 1103, activity 1104, activity 1201, and/or activity 1202 can be performed using a processing module. The processing module can be similar or identical to processing module 190 (FIG. 1). In some embodiments, activity 803, activity 804, and activity 805 can be performed multiple times for multiple electromagnetic frequencies of the electromagnetic waves.

Figure 13:
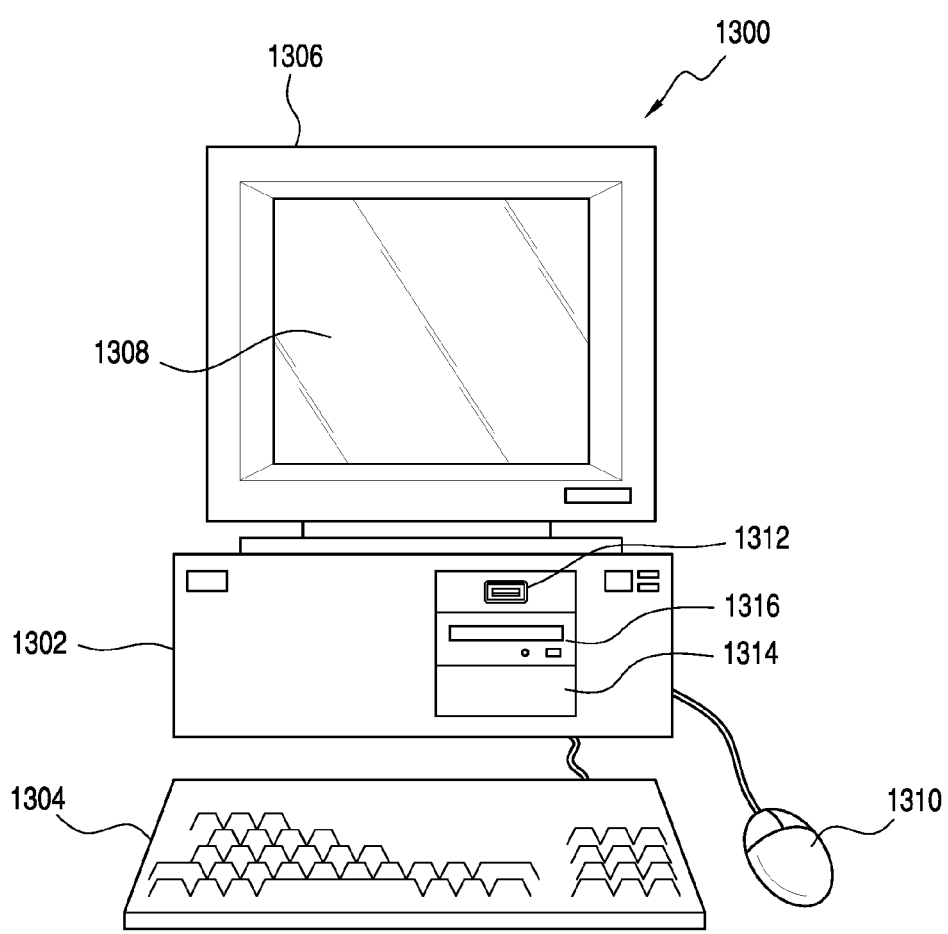
FIG. 13 illustrates an exemplary computer system that is suitable for implementing an embodiment of a computer system of the apparatus of FIG. 1, the method of FIG. 8, and/or the activity of FIG. 12.
Figure 14:
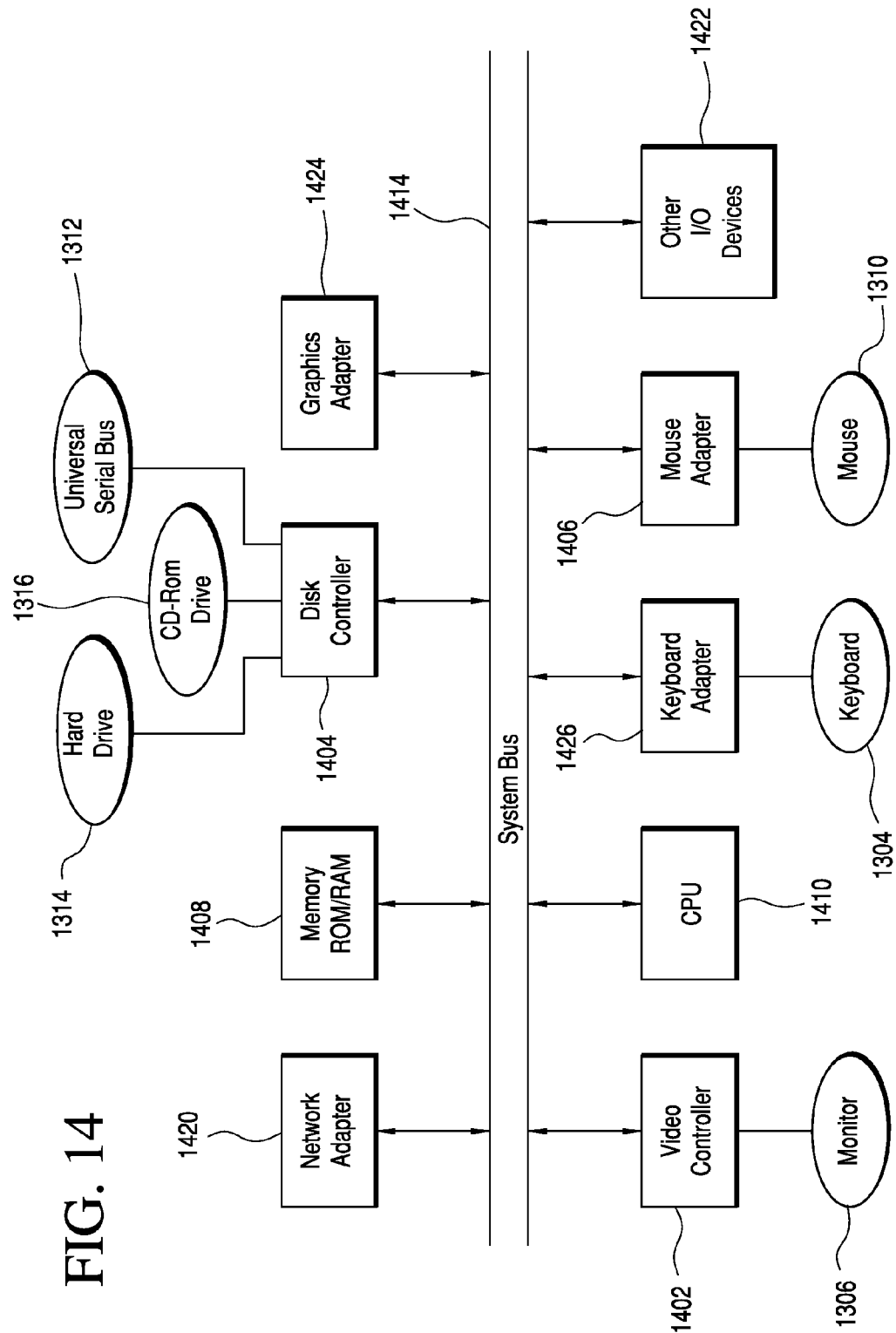
FIG. 14 illustrates a representative block diagram of an example of the elements included in the circuit boards inside a chassis of the computer system of FIG. 13.

Turning ahead now in the drawings, FIG. 13 illustrates a computer system 1300 that is suitable for implementing an embodiment of at least a portion of the computer system of apparatus 100 (FIG. 1) and/or for performing at least part of method 800 (FIG. 8). Computer 1300 includes a chassis 1302 containing one or more circuit boards (not shown), a USB (universal serial bus) port 1312, a Compact Disc Read-Only Memory (CD-ROM) and/or Digital Video Disc (DVD) drive 1316, and a hard drive 1314. A representative block diagram of the elements included on the circuit boards inside chassis 1302 is shown in FIG. 14. A central processing unit (CPU) 1410 in FIG. 14 is coupled to a system bus 1414 in FIG. 14. In various embodiments, the architecture of CPU 1410 can be compliant with any of a variety of commercially distributed architecture families.

System bus 1414 also is coupled to memory 1408 that includes both read only memory (ROM) and random access memory (RAM). Non-volatile portions of memory 1408 or the ROM can be encoded with a boot code sequence suitable for restoring computer system 1300 (FIG. 13) to a functional state after a system reset. In addition, memory 1408 can include microcode such as a Basic Input-Output System (BIOS). In some examples, memory 1108, USB in USB port 1112, hard drive 1114, and/or CD-ROM or DVD drive 1116 can be part of a storage module of computer system 1300. Storage module 191 (FIG. 1) can be similar or identical to the storage module of computer system 1300 (FIG. 13).

In the depicted embodiment of FIG. 14, various I/O devices such as a disk controller 1404, a graphics adapter 1424, a video controller 1402, a keyboard adapter 1426, a mouse adapter 1406, a network adapter 1420, and other I/O devices 1422 can be coupled to system bus 1414. Keyboard adapter 1426 and mouse adapter 1406 are coupled to a keyboard 1304 (FIGS. 13 and 14) and a mouse 1310 (FIGS. 13 and 14), respectively, of computer system 1300 (FIG. 13). While graphics adapter 1424 and video controller 1402 are indicated as distinct units in FIG. 14, video controller 1402 can be integrated into graphics adapter 1424, or vice versa in other embodiments. Video controller 1402 is suitable for refreshing a monitor 1306 (FIGS. 13 and 14) to display images on a monitor 1306 (FIG. 13) of computer system 1300 (FIG. 13). Disk controller 1404 can control hard drive 1314 (FIGS. 13 and 14), USB port 1312 (FIGS. 13 and 14), and CD-ROM or DVD drive 1316 (FIGS. 13 and 14). In other embodiments, distinct units can be used to control each of these devices separately.

Although many other components of computer system 1300 (FIG. 13) are not shown, such components and their interconnection are well known to those of ordinary skill in the art. Accordingly, further details concerning the construction and composition of computer system 1300 and the circuit boards inside chassis 1302 (FIG. 13) need not be discussed herein.

When computer system 1300 in FIG. 13 is running, program instructions stored on stored on a USB drive in USB port 1312, on a CD-ROM or DVD in CD-ROM and/or DVD drive 1316, on hard drive 1314, or in memory 1408 (FIG. 14) are executed by CPU 1410 (FIG. 14). A portion of the program instructions, stored on these devices, can be suitable for carrying out at least part of method 800 (FIG. 8).

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that any of the activities of method 800 (FIG. 8) and/or of activity 1300 (FIG. 10) may be comprised of many different activities and be performed by many different modules, and in many different orders, that any element of FIGS. 1-14 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A system for determining one or more parameters related to one or more electromagnetic fields in electrical cavities, the system comprising:
   a first cavity;
   a second cavity coupled to the first cavity;
   at least one electromagnetic wave creation element located in the second cavity;
   a processing module; and
   a non-transitory memory storage module storing computer instructions configured to run on the processing module and perform acts of:
      receiving two or more measurement parameters related to the first cavity and the second cavity;
      receiving one or more electrical parameters of the at least one electromagnetic wave creation element;
      determining an energy matrix of one or more electromagnetic fields in the first cavity and the second cavity;
      determining a mean energy of the one or more electromagnetic fields in the first cavity and the second cavity; and
      determining an energy variance of the one or more electromagnetic fields in the first cavity and the second cavity.

2. The apparatus of claim 1 wherein the acts further comprise:
   using the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element.

3. The apparatus of claim 2 wherein the acts further comprise:

determining a model of the one or more potential changes to the at least one of (i) the first cavity, (ii) the second cavity, or (iii) the at least one electromagnetic wave creation element.

4. The apparatus of claim 3 further comprising:
a display device coupled to the processing module;
wherein:
the acts further comprise displaying the model at the display device.

5. The apparatus of claim 1 wherein:
the first cavity comprises a first room in an immobile structure;
the second cavity comprises a second room in the immobile structure; and
the first room is coupled to the second room via an aperture.

6. The apparatus of claim 1 wherein one of:
the first cavity comprises a cockpit of a first aircraft, the second cavity comprises a cabin of the first aircraft, and the cabin is coupled to the cockpit via a first aperture;
the first cavity comprises a first room in a ship, the second cavity comprises a second room in the ship, and the first room is coupled to the second room via a second aperture;
the first cavity comprises a region exterior to a second aircraft, and the second cavity comprises an interior of the second aircraft; or
the first cavity comprises a first compartment of a vehicle, and the second cavity comprises a second compartment of the vehicle.

7. The apparatus of claim 1 wherein:
the at least one electromagnetic wave creation element comprises at least one of a mobile communications device, an electromagnetic pulse weapon, or lightning.

8. A method of determining one or more electromagnetic fields in a first cavity coupled to a second cavity, at least one electromagnetic wave creation element being located in the second cavity and an electrical system comprising the first cavity, the second cavity, and the at least one electromagnetic wave creation element, the method comprises:
determining two or more physical parameters of the first cavity and the second cavity;
determining one or more electrical parameters of the at least one electromagnetic wave creation element;
executing one or more first computer instructions configured to determine an energy matrix for the electrical system;
executing one or more second computer instructions configured to determine a mean energy of the one or more electromagnetic fields in the first cavity and the second cavity; and
executing one or more third computer instructions configured to determine an energy variance of the one or more electromagnetic fields in the first cavity and the second cavity;
wherein:
the one or more first computer instructions, the one or more second computer instructions, and the one or more third computer instructions are configured to run at a processing module and configured to be stored at a non-transitory memory storage module.

9. The method of claim 8 further comprising:
executing one or more fourth computer instructions configured to use the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element;
wherein:
the one or more fourth computer instructions are configured to run at the processing module and configured to be stored at the non-transitory memory storage module.

10. The method of claim 9 wherein:
the one or more potential changes comprise at least one of:
adding electromagnetic shielding to at least one electrical component located in at least one of the first cavity or the second cavity; or
moving the at least one electrical component located in the at least one of the first cavity or the second cavity.

11. The method of claim 8 further comprising:
executing one or more fourth computer instructions configured to determine a model of the one or more electromagnetic fields in the first cavity based upon (i) the mean energy of the one or more electromagnetic fields in the first cavity and the second cavity and (ii) the energy variance of the one or more electromagnetic fields in the first cavity and the second cavity;
wherein:
the one or more fourth computer instructions are configured to run at the processing module and configured to be stored at the non-transitory memory storage module.

12. The method of claim 11 wherein:
executing the one or more fourth computer instructions comprises:
executing one or more fifth computer instructions configure to determine confidence bands of a maximum energy of the one or more electromagnetic fields in the first cavity; and
executing one or more sixth computer instructions configure to determine a probability that the maximum energy of the one or more electromagnetic fields in the first cavity is equal to or greater than a predetermined energy level.

13. The method of claim 8 wherein:
determining the two or more physical parameters of the first cavity and the second cavity comprises at least one of:
measuring at least part of one or more dimensions of the first cavity and the second cavity;
using design drawings of the first cavity and the second cavity to determine the one or more dimensions of the first cavity and the second cavity;
determining one or more dimensions of an aperture between the first cavity and the second cavity; or
determining reflective properties at least one of one or more surfaces of the first cavity and the second cavity or one or more coatings on at least one surface of the one or more surfaces.

14. The method of claim 8 wherein:
determining the one or more electrical parameters of the at least one electromagnetic wave creation element comprises at least one of:
determining an electric power of one or more frequencies of electromagnetic waves emitted by the at least one electromagnetic wave creation element;
determining at least one frequency of interest from the one or more frequencies of the electromagnetic waves emitted by the at least one electromagnetic wave creation element; or determining at least one wave length of the electromagnetic waves emitted by the at least one electromagnetic wave creation element.

15. The method of claim 8 wherein:

executing the one or more first computer instructions comprises:

executing one or more fourth computer instructions configured to determine a loss factor for each of the first cavity and the second cavity;

executing one or more fifth computer instructions configured to determine coupling loss factors for the first cavity and the second cavity; and executing one or more sixth computer instructions configured to determine a cavity modal density for each of the first cavity and the second cavity.

16. The method of claim 8 wherein:

executing the one or more second computer instructions comprises:

executing one or more fourth computer instructions configured to determine a loading factor for each of the first cavity and the second cavity;

executing one or more fifth computer instructions configured to determine a coupling factor for each pair of the first cavity and the second cavity that are coupled together;

executing one or more sixth computer instructions configured to determine an effective modal overlap factor for each of the first cavity and the second cavity; and executing one or more seventh computer instructions configured to determine the energy variance at an average energy of two or more emitted frequencies;

and the one or more electromagnetic fields comprise electromagnetic waves at the two or more emitted frequencies.

17. The method of claim 8 wherein:

executing the one or more third computer instructions comprises:

executing one or more fourth computer instructions configured to invert the energy matrix to determine the mean energy of the one or more electromagnetic fields in the first cavity and the second cavity.

18. A method of determining one or more electromagnetic fields in a first cavity coupled to a second cavity, at least one electromagnetic wave creation element being located in the second cavity and an electrical system comprising the first cavity, the second cavity, and the at least one electromagnetic wave creation element, the method comprises:

executing one or more first computer instructions configured to identify two or more physical parameters of the first cavity and the second cavity;

executing one or more second computer instructions configured to identify one or more electrical parameters of the at least one electromagnetic wave creation element;

executing one or more third computer instructions configured to determine a mean energy of the one or more electromagnetic fields in the first cavity and the second cavity;

executing one or more fourth computer instructions configured to determine an energy variance of the one or more electromagnetic fields in the first cavity and the second cavity;

executing one or more fifth computer instructions configured to use the mean energy of the one or more electromagnetic fields in the first cavity and the second cavity and the energy variance of the one or more electromagnetic fields in the first cavity and the second cavity to determine one or more potential changes to at least one of (i) the first cavity, (ii) the second cavity, or (iii) the at least one electromagnetic wave creation element; and executing one or more sixth computer instructions configured to model the one or more potential changes;

wherein:

the one or more first computer instructions, the one or more second computer instructions, the one or more third computer instructions, the one or more fourth computer instructions, the one or more fifth computer instructions, and the one or more sixth computer instructions are configured to run at a processing module and configured to be stored at a non-transitory memory storage module.

\* \* \* \* \*